(12) United States Patent
Shintou et al.

(10) Patent No.: US 10,220,024 B2
(45) Date of Patent: Mar. 5, 2019

(54) METHOD OF INHIBITING CANCER CELL, METHOD FOR DETECTING CANCER CELL, AND SYSTEM FOR DETECTING CANCER CELL

(71) Applicant: CANON KABUSHIKI KAISHA, Tokyo (JP)

(72) Inventors: Taichi Shintou, Saitama (JP); Tsuyoshi Nomoto, Tokyo (JP); Kohei Watanabe, Brookline, MA (US); Takeshi Miyazaki, Ebina (JP); Toshio Tanaka, Tsu (JP); Yasuhito Shimada, Tsu (JP); Yuhei Nishimura, Tsu (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/351,683

(22) Filed: Nov. 15, 2016

(65) Prior Publication Data

US 2017/0056378 A1    Mar. 2, 2017

Related U.S. Application Data

(62) Division of application No. 14/408,778, filed as application No. PCT/JP2013/079651 on Oct. 25, 2013, now abandoned.

(30) Foreign Application Priority Data

Oct. 26, 2012  (JP) .................................. 2012-236981

(51) Int. Cl.
| | | |
|---|---|---|
| A61K 31/404 | (2006.01) |
| A61K 31/4184 | (2006.01) |
| A61K 31/423 | (2006.01) |
| A61K 31/428 | (2006.01) |
| A61K 41/00 | (2006.01) |
| A61K 49/00 | (2006.01) |
| A61K 31/403 | (2006.01) |
| C07D 417/06 | (2006.01) |
| C07D 417/14 | (2006.01) |
| A61K 31/427 | (2006.01) |

(52) U.S. Cl.
CPC .......... *A61K 31/428* (2013.01); *A61K 31/403* (2013.01); *A61K 31/404* (2013.01); *A61K 31/423* (2013.01); *A61K 31/427* (2013.01); *A61K 41/0038* (2013.01); *A61K 49/0032* (2013.01); *C07D 417/06* (2013.01); *C07D 417/14* (2013.01)

(58) Field of Classification Search
CPC .............. A61K 31/404; A61K 31/4184; A61K 31/423; A61K 31/428; A61K 49/0032
USPC ................ 514/415, 414, 409, 394, 375, 367
See application file for complete search history.

(56) References Cited

U.S. PATENT DOCUMENTS

| | | |
|---|---|---|
| 7,622,479 B2 | 11/2009 | Oda et al. |
| 8,652,438 B2 | 2/2014 | Nomoto et al. |
| 2002/0086344 A1 | 7/2002 | Tsuji et al. |
| 2005/0042213 A1 | 2/2005 | Gelder et al. |
| 2011/0182810 A1 | 7/2011 | Nomoto et al. |
| 2011/0189096 A1 | 8/2011 | Watanabe et al. |
| 2011/0243850 A1 | 10/2011 | Shintou et al. |
| 2012/0207683 A1 | 8/2012 | Tanaka et al. |
| 2012/0208204 A1 | 8/2012 | Baldwin et al. |
| 2013/0280169 A1 | 10/2013 | Watanabe et al. |
| 2014/0017722 A1 | 1/2014 | Watanabe et al. |
| 2014/0094490 A1 | 4/2014 | Ohta et al. |
| 2014/0112869 A1 | 4/2014 | Nomoto et al. |
| 2015/0157745 A1 | 6/2015 | Shintou et al. |
| 2015/0182518 A1 | 7/2015 | Shintou et al. |

FOREIGN PATENT DOCUMENTS

| | | |
|---|---|---|
| EP | 2 397 139 A1 | 12/2011 |
| JP | 2003-221386 A | 8/2003 |
| JP | 2010-013380 A | 1/2010 |
| JP | 2010-169678 | 8/2010 |
| JP | 2010-269666 A | 8/2010 |
| KR | 10-2010-0102273 A | 9/2010 |

(Continued)

OTHER PUBLICATIONS

Harriman, A, L. Shoute, and P. Neta "Radiation Chemistry of Cyanine Dyes: Oxidation and Reduction of Merocyanine 540" Journ. Phys. Chem. (1991), 95(6), pp. 2415-2420.*
Chem. Abstract Database Accession No. 2010:1211901 (Sep. 2010) (XP002740524).
Chem. Abstract Database Accession No. 76433-29-9 (Nov. 1984) (XP002740525).
Extended European Search Report in European Application No. 13849471.1 (dated Jun. 18, 2015).

(Continued)

*Primary Examiner* — Matthew P Coughlin
*Assistant Examiner* — Sagar Patel
(74) *Attorney, Agent, or Firm* — Venable LLP

(57) ABSTRACT

An object of the present invention is to provide a cancer cell inhibitory drug, particularly a cancer stem-cell inhibitory drug, or a cancer stem-cell detection probe. A cancer cell inhibitory drug containing at least a compound represented by general formula (1).

General Formula (1)

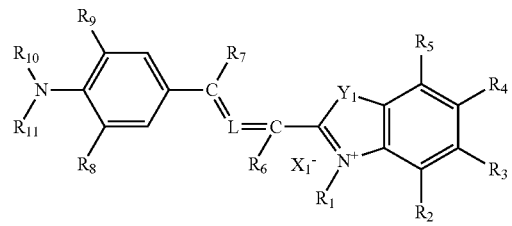

20 Claims, No Drawings

(56) References Cited

FOREIGN PATENT DOCUMENTS

| WO | 00/30632 A1 | 6/2000 | | |
|---|---|---|---|---|
| WO | 02/35474 A1 | 5/2002 | | |
| WO | 2010/074325 A1 | 7/2010 | | |
| WO | 2010/074326 A1 | 7/2010 | | |
| WO | WO 2010074325 A1 | * | 7/2010 | ......... A61K 49/0002 |
| WO | 2011/017219 A1 | 2/2011 | | |
| WO | 2014/065439 A1 | 5/2014 | | |

OTHER PUBLICATIONS

Fariba Behbod et al., "Will Cancer Stem Cells Provide New Therapeutic Targets?" 26(4) Carcinogenesis 703-711 (2004).

Michael Dean et al., "Tumour Stem Cells and Drug Resistance," 5(4) Nature Reviews Cancer 275-284 (Apr. 2005).

Masujiro Katayanagi, "Preparation of Styryl Dyes from Aromatic Heterocyclic Ammonium Salts. X," 69(5) Yakugaku Zasshi 237-240 (1949).

S. Mohanty et al., "Effect of Structural Changes in the Chromophoric Chain on Absorption of Dyes Derived from Benzthiazole," 6 Indian J. Chem. 136-139 (Mar. 1968).

V. Dryanska et al., "α-Hydroxybenzylation and Benzylidenation of the Methyl Group in 2-Methyl-1,3-benzoxazole and 2-Methyl-1,3-benzothiazole," 1976(1) Synthesis 37-38 (Jan. 1976).

Iryna A. Fedyunyayeva et al., "The Synthesis, Structure and Spectral Properties of New Long-Wavelength Benzodipyrroleninium-Based Bis-Styryl Dyes," 90(2) Dyes and Pigments 201-210 (Dec. 2010).

International Search Report in International Application No. PCT/JP2013/079651 (dated Nov. 2013).

Written Opinion in International Application No. PCT/JP2013/079651 (dated Nov. 2013).

International Preliminary Report on Patentability in International Application No. PCT/JP2013/079651 (dated Apr. 2015).

Notification of Reasons for Refusal in Japanese Application No. 2013-222030 (Oct. 19, 2017).

* cited by examiner

METHOD OF INHIBITING CANCER CELL, METHOD FOR DETECTING CANCER CELL, AND SYSTEM FOR DETECTING CANCER CELL

CROSS-REFERENCE TO RELATED APPLICATIONS

This application is a divisional application of U.S. patent application Ser. No. 14/408,778, which was the National Stage of International Application No. PCT/JP2013/079651, filed Oct. 25, 2013, which claims the benefit of Japanese Patent Application No. 2012-236981, filed Oct. 26, 2012. All of these prior applications are incorporated herein by reference in their entirety.

TECHNICAL FIELD

The present invention relates to a cancer cell inhibitory drug, particularly to a cancer stem cell inhibitory drug, and a cancer stem-cell detection probe.

BACKGROUND ART

At present, as a general cancer therapy, e.g., radiation therapy, chemotherapy, immunotherapy and surgical (excision) therapy are mentioned. The chemotherapy is a method for suppressing cancer by use of an anticancer therapeutic agent made of various types of low-molecular compounds.

The therapy using an anticancer therapeutic agent is directed to reduce the size of a solid tumor. However, the most part of a tumor is occupied by differentiated cancer cells which no longer have a function as a cancer stem cell and it is pointed out in a general anticancer agent treatment that the differentiated cancer cells are only targeted to reduce the size thereof.

Cancer has cells having nature of stem cells, called cancer stem cells. The cancer stem cells, which were first identified in 1997 in an acute myeloid leukemia, are now increasingly found in various types of cancers including solid cancers, and recently, a new way of thinking, called "cancer stem cell hypothesis" that cancer would be developed from cancer stem cells as an origin, has been proposed (NPL 1).

According to the hypothesis, even though the most part of cancer cells are killed or excised out by applying the aforementioned therapy, if a very small number of self-reproducible cancer stem cells remain, recurrence and metastasis conceivably occur. In short, it is considered that recurrence and metastasis are caused by the remaining small amount of cancer stem cells. Accordingly, if cancer stem cells can be targeted and completely eradicated, it is expected to develop a useful therapy for preventing metastasis and recurrence of cancer.

It is pointed out that some of the cancer stem cells acquire drug resistance to an anticancer therapeutic agent (NPL 2).

At present, as a low-molecular compound for use in detection of cancer stem cells and as a therapeutic agent, a compound containing radioactive Cu-ATSM is known (PTL 1). However, the radioactive compound may affect normal cells. Therefore, when a radioactive compound is used, safety becomes a matter of concern. In addition, it is also pointed out that cancer stem cells may develop strong resistance to radiation.

In the circumstances, it has been desired to develop a drug inhibiting cancer stem cells and a compound capable of detecting cancer stem cells.

CITATION LIST

Patent Literature

PTL 1: Japanese Patent Application Laid-Open No. 2010-13380
PTL 2: Japanese Patent Application Laid-Open No. 2010-169678

Non Patent Literature

NPL 1: Carcinogenesis, Vol.26, p.p. 703-711, 2005
NPL 2: Nature Review Cancer., Vol.5, p.p. 275-284, 2005
NPL 3: Yakugaku Zasshi, Vol.69, p.p.237-239, 1949
NPL 4: Indian Journal of Chemistry, Vol.6, p.p.136-139, 1968
NPL 5: Synthesis, p.p.37-38, 1976
NPL 6: Dye and Pigments, Vol.90, p.p.201-210, 2011

SUMMARY OF INVENTION

Technical Problem

Cancer stem cells have high resistance to radiation therapies and chemotherapies conventionally used and are causual cells from which cancer growth, recurrence and metastasis occur. Up to present, where cancer stem cells are present cannot be clearly detected. This was a issue remaining unsolved. To completely cure cancer, it has been strongly desired to detect cancer stem cells and develop a drug inhibiting cancer cells, in particular, cancer stem cells.

Solution to Problem

The present inventors intensively made studies with a view to solving the aforementioned problem. As a result, they found that a compound represented by the following general formula (1) has an inhibitory effect on cancer cells and is selectively taken into particularly cancer stem cells among the cancer cells and inhibits them. Based on the finding, the present invention was accomplished.

Furthermore, the compound of the present invention has a luminescence property. Owing to this, the position of cancer cells can be identified (determined) by detecting luminescence of the compound selectively taken into cancer cells. Based on the finding, the present inventors arrived at the present invention. Note that, in the specification, luminescence includes fluorescence and phosphorescence. Since the compound of the present invention is taken into particularly cancer stem cells in a high ratio, cancer stem cells can be selectively detected.

More specifically, the compound of the present invention contains a compound represented by general formula (1):

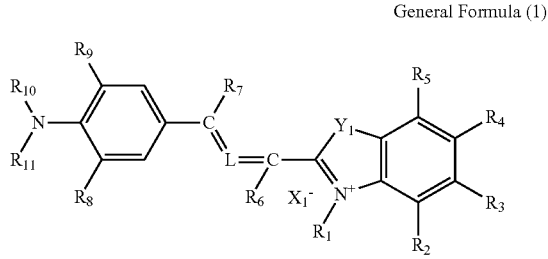

General Formula (1)

In general formula (1), $R_1$ independently represents an alkyl group, a carboxylalkyl group, an alkoxycarbonylalkyl group or an alkylcarbonyloxyalkyl group; and $R_2$ to $R_5$ each independently represent a hydrogen atom, an alkyl group, an aryl group, an alkoxy group, a halogen atom, an alkoxysulfonyl group, a N-alkylsulfamoyl group, an alkyloxycarbonyl group or a N-alkylcarbamoyl group. $R_6$ and $R_7$ each independently represent a hydrogen atom, an alkyl group or a phenyl group; $R_8$ and $R_9$ each independently represent a hydrogen atom, an alkyl group, an alkenyl group or a halogen atom; and $R_{10}$ and $R_{11}$ each independently represent an alkyl group, an aryl group or an aralkyl group. $R_9$ and $R_{10}$ may bind together to form a nitrogen atom-containing hetero ring. $X_1^-$ represents an anionic group.

$Y_1$ represents an oxygen atom, a sulfur atom, a nitrogen atom binding to an alkyl group or —$C(R_{12})(R_{13})$— where $R_{12}$ and $R_{13}$ each independently represent an alkyl group. $R_{12}$ and $R_{13}$ may bind together to form an aliphatic ring.

L is absent (in this case, carbons at both sides of L are bound via a double bond), represented by general formula (2) or represents =$C(R_{15})$—$C(R_{16})$= where $R_{15}$ and $R_{16}$ each independently represent a hydrogen atom or an alkyl group.

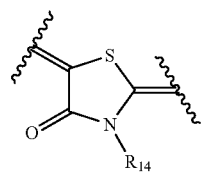

General Formula (2)

In general formula (2), $R_{14}$ represents an alkyl group, a carboxylalkyl group, an alkoxycarbonylalkyl group or an alkylcarbonyloxyalkyl group.

Advantageous Effects of Invention

Owing to the cancer cell inhibitory drug provided by the present invention, growth suppression, cellular division suppression, metastasis suppression, functional inhibition and cytocidal action of cancer cells can be mediated even in sites where cancer cells are overlooked by surgical excision and hardly excised out. Of the cancer cells, particularly against cancer stem cells, these effects are significantly exerted. Furthermore, cancer stem cells can be easily detected and the site of the cancer stem cells can be accurately determined. More specifically, the present invention provides a cancer stem-cell detection probe.

DESCRIPTION OF EMBODIMENTS

Now, embodiments of the present invention will be described below.

The compound of the present invention is effective as a cancer cell inhibitory drug. Particularly, the compound of the present invention is selectively taken into cancer stem cells among cancer cells, thereby inhibiting them. Furthermore, the compound of the present invention is effective as a cancer stem-cell detection probe.

The cancer cell inhibitory drug has an effect of inhibiting growth and survival of cancer cells. The cancer stem-cell detection probe is selectively taken into cancer stem cells and successfully detects the cancer stem cells.

Cancer Cell Inhibitory Drug

According to a first embodiment of the present invention, the cancer cell inhibitory drug contains a compound represented by general formula (1).

The cancer cell inhibitory drug refers to a composition having functions of suppressing growth, cellular division, metastasis and function of cancer cells and killing cancer cells. Furthermore, cancer cells can be detected and observed by measuring luminescence of the compound of the present invention.

Compound represented by general formula (1)

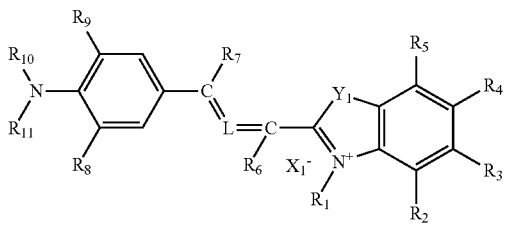

General Formula (1)

In general formula (1), $R_1$ independently represents an alkyl group, a carboxylalkyl group, an alkoxycarbonylalkyl group or an alkylcarbonyloxyalkyl group; and $R_2$ to $R_5$ each independently represent a hydrogen atom, an alkyl group, an aryl group, an alkoxy group, a halogen atom, an alkoxysulfonyl group, a N-alkylsulfamoyl group, an alkyloxycarbonyl group or a N-alkylcarbamoyl group. $R_6$ and $R_7$ each independently represent a hydrogen atom, an alkyl group or a phenyl group; $R_8$ and $R_9$ each independently represent a hydrogen atom, an alkyl group, an alkenyl group or a halogen atom; and $R_{10}$ and $R_{11}$ each independently represent an alkyl group, an aryl group or an aralkyl group. $R_9$ and $R_{10}$ may bind together to form a nitrogen atom-containing hetero ring. $X_1^-$ represents an anionic group.

$Y_1$ represents an oxygen atom, a sulfur atom, a nitrogen atom binding to an alkyl group or —$C(R_{12})(R_{13})$— where $R_{12}$ and $R_{13}$ each independently represent an alkyl group. $R_{12}$ and $R_{13}$ may bind together to form an aliphatic ring.

L is absent (in this case, carbons at both sides of L are bound via a double bond), represented by general formula (2) or represents =$C(R_{15})$—$C(R_{16})$= where $R_{15}$ and $R_{16}$ each independently represent a hydrogen atom or an alkyl group.

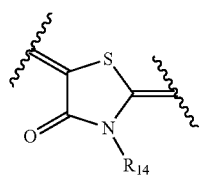

General Formula (2)

In general formula (2), $R_{14}$ represents an alkyl group, a carboxylalkyl group, an alkoxycarbonylalkyl group or an alkylcarbonyloxyalkyl group.

In general formula (1), examples of the alkyl group represented by $R_1$ include, but are not particularly limited to, a methyl group, an ethyl group, a propyl group, a butyl group, a pentyl group and a hexyl group.

In general formula (1), examples of the carboxylalkyl group represented by $R_1$ include, but are not particularly limited to, a carboxylmethyl group, a carboxylethyl group and a carboxylpropyl group.

In general formula (1), examples of the alkoxycarbonylalkyl group represented by $R_1$ include, but are not particularly limited to, a methoxycarbonylmethyl group, a methoxycarbonylethyl group, an ethoxycarbonylethyl group, a butoxycarbonylethyl group and a methoxycarbonylpropyl group; and Examples of the alkylcarbonyloxyalkyl group include, but are not particularly limited to, a methylcarbonyloxymethyl group, an ethylcarbonyloxymethyl group, an ethylcarbonyloxyethyl group, an ethylcarbonyloxybutyl group and a propylcarbonyloxymethyl group.

In general formula (1), examples of the alkyl groups represented by $R_2$ to $R_5$ include, but are not particularly limited to, a methyl group, an ethyl group, a propyl group, a butyl group, a pentyl group and a hexyl group.

In general formula (1), examples of the aryl groups represented by $R_2$ to $R_5$ include, but are not particularly limited to, a phenyl group, a 2-bromophenyl group, a 3-bromophenyl group, a 4-bromophenyl group, a 2-methoxyphenyl group, a 3-methoxyphenyl group, a 4-methoxyphenyl group, a 2-thiomethylphenyl group, a 3-thiomethylphenyl group, a 4-thiomethylphenyl group and a naphthyl group.

In general formula (1), examples of the alkoxy groups represented by $R_2$ to $R_5$ include, but are not particularly limited to, a methoxy group, an ethoxy group, a propoxy group and a butoxy group.

In general formula (1), examples of the halogen atoms represented by $R_2$ to $R_5$ include a fluorine atom, a chlorine atom, a bromine atom and an iodine atom.

In general formula (1), examples of the alkoxysulfonyl groups represented by $R_2$ to $R_5$ include, but are not particularly limited to, a methoxysulfonyl group and an ethoxysulfonyl group.

In general formula (1), examples of the N-alkylsulfamoyl groups represented by $R_2$ to $R_5$ include, but are not particularly limited to, a N-methylsulfamoyl group, a N-ethylsulfamoyl group, a N,N-dimethylsulfamoyl group and a N,N-diethylsulfamoyl group.

In general formula (1), examples of the alkyloxycarbonyl groups represented by $R_2$ to $R_5$ include, but are not particularly limited to, a methyloxycarbonyl group, an ethyloxycarbonyl group, a propyloxycarbonyl group and a butyloxycarbonyl group.

In general formula (1), examples of the N-alkylcarbamoyl groups represented by $R_2$ to $R_5$ include, but are not particularly limited to, a N-methylcarbamoyl group, a N-ethylcarbamoyl group, a N,N-dimethylcarbamoyl group and a N,N-diethylcarbamoyl group.

$R_2$ to $R_5$ each independently represent preferably a hydrogen atom, a halogen atom, a phenyl group or an alkoxy group, and more preferably a hydrogen atom or a phenyl group.

In general formula (1), examples of the alkyl groups represented by $R_6$ and $R_7$ include, but are not particularly limited to, a methyl group, an ethyl group, a propyl group and a butyl group.

In general formula (1), examples of the alkyl groups and alkenyl groups represented by $R_8$ and $R_9$ include, but are not particularly limited to, a methyl group, an ethyl group, a propyl group, a butyl group, a methylene group, an ethylene group and a propylene group. Furthermore, the side chains of the alkyl group and alkenyl group may be further substituted with an alkyl group, an alkenyl group and the like.

In general formula (1), examples of the halogen atoms represented by $R_8$ and $R_9$ include a fluorine atom, a chlorine atom, a bromine atom and an iodine atom.

In general formula (1), examples of the alkyl groups represented by $R_{10}$ and $R_{11}$ include, but are not particularly limited to, a methyl group, an ethyl group, a propyl group, a butyl group, a pentyl group, a hexyl group and a 2-ethylhexyl group.

In general formula (1), examples of the aryl groups represented by $R_{10}$ and $R_{11}$ include, but are not particularly limited to, a phenyl group, a 2-bromophenyl group, a 3-bromophenyl group, a 4-bromophenyl group, a 2-methoxyphenyl group, a 3-methoxyphenyl group, a 4-methoxyphenyl group, a 2-methylthiophenyl group, a 3-methylthiophenyl group, a 4-methylthiophenyl group and a naphthyl group. Alternatively, groups represented by general formula (6) are mentioned. In general formula (6), reference symbol * represents a binding site.

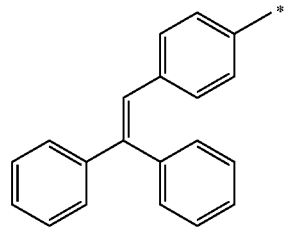

General Formula (6)

In general formula (1), examples of the aralkyl groups represented by $R_{10}$ and $R_{11}$ include, but are not particularly limited to, a benzyl group and a phenethyl group.

In general formula (1), examples of the nitrogen atom-containing hetero ring formed by binding $R_9$ and $R_{10}$ together include, but are not particularly limited to, a pyrrolidine ring, a pyrrole ring, a pyrrolidine ring, an indole ring and a cyclopentapyrrole ring.

In general formula (1), examples of the anionic group represented by $X_1^-$ include, but are not particularly limited to, a chloride ion, a bromide ion, an iodide ion, a sulfate ion, a nitrate ion and a methanesulfonate ion.

In general formula (1), examples of the alkyl group of the nitrogen atom binding to an alkyl group represented by $Y_1$ include, but are not particularly limited to, a methyl group, an ethyl group, a propyl group and a butyl group.

In general formula (1), examples of the alkyl groups represented by $R_{12}$ and $R_{13}$ in $Y_1$ include, but are not particularly limited to, a methyl group, an ethyl group, a propyl group, a butyl group, a pentyl group, a hexyl group and a 2-ethylhexyl group. $R_{12}$ and $R_{13}$ are favorably the same substituents.

In general formula (1), examples of the aliphatic ring formed by binding $R_{12}$ and $R_{13}$ together in $Y_1$, include, but are not particularly limited to, a cyclohexane ring and a cyclopentane ring.

In general formula (1), examples of the alkyl groups represented by $R_{15}$ and $R_{16}$ in L include, but are not particularly limited to, a methyl group, an ethyl group, a propyl group, a butyl group, a pentyl group, a hexyl group and 2-ethylhexyl group.

In general formula (2), examples of the alkyl group represented by $R_{14}$ include, but are not particularly limited to, a methyl group, an ethyl group, a propyl group, a butyl group, a pentyl group, a hexyl group and a 2-ethylhexyl group.

In general formula (2), examples of the carboxylalkyl group represented by $R_{14}$ include, but are not particularly limited to, a carboxylmethyl group, a carboxylethyl group and a carboxylpropyl group.

In general formula (2), examples of the alkoxycarbonylalkyl group represented by $R_{14}$ include, but are not particularly limited to, a methoxycarbonylmethyl group, a methoxycarbonylethyl group, an ethoxycarbonylethyl group, a butoxycarbonylethyl group and a methoxycarbonyl propyl group; and Examples of the alkylcarbonyloxyalkyl group include, but are not particularly limited to, a methylcarbonyloxymethyl group, an ethylcarbonyloxymethyl group, an ethylcarbonyloxyethyl group, an ethylcarbonyloxybutyl group and a propylcarbonyloxymethyl group.

Compound represented by general formula (3) As a favorable compound of the present invention, a compound represented by general formula (3) can be mentioned.

General Formula (3)

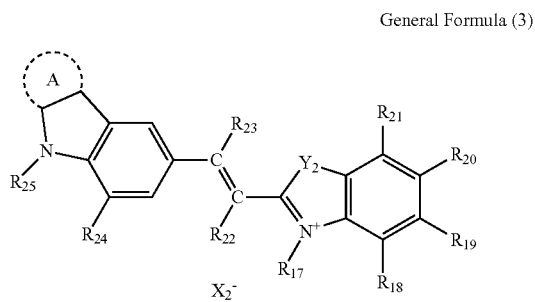

In general formula (3), $R_{17}$ each independently represents an alkyl group, a carboxylalkyl group, an alkoxycarbonylalkyl group or an alkylcarbonyloxyalkyl group; and $R_{18}$ to $R_{21}$ each independently represent a hydrogen atom, an alkyl group, an aryl group, an alkoxy group, a halogen atom, an alkoxysulfonyl group, a N-alkylsulfamoyl group, an alkyloxycarbonyl group or a N-alkylcarbamoyl group. $R_{22}$ and $R_{23}$ each independently represent a hydrogen atom, an alkyl group or a phenyl group; $R_{24}$ represents a hydrogen atom or a halogen atom; and $R_{25}$ represents an alkyl group, an aryl group or an aralkyl group. $X_2^-$ represents an anionic group.

$Y_2$ represents an oxygen atom, a sulfur atom, a nitrogen atom binding to an alkyl group or —$C(R_{26})(R_{27})$— where $R_{26}$ and $R_{27}$ each independently represent an alkyl group. $R_{26}$ and $R_{27}$ may bind together to form an aliphatic ring.

Reference symbol A represents a cyclopentane ring or a benzene ring.

In general formula (3), examples of the alkyl group represented by $R_{17}$ include, but are not particularly limited to, a methyl group, an ethyl group, a propyl group, a butyl group, a pentyl group and a hexyl group.

In general formula (3), examples of the carboxylalkyl group represented by $R_{17}$ include, but are not particularly limited to, a carboxylmethyl group, a carboxylethyl group and a carboxylpropyl group.

In general formula (3), examples of the alkoxycarbonylalkyl group represented by $R_{17}$ include, but are not particularly limited to, a methoxycarbonylmethyl group, a methoxycarbonylethyl group, an ethoxycarbonylethyl group, a butoxycarbonylethyl group and a methoxycarbonylpropyl group; and Examples of the alkylcarbonyloxyalkyl group include, but are not particularly limited to, a methylcarbonyloxymethyl group, an ethylcarbonyloxymethyl group, an ethylcarbonyloxyethyl group, an ethylcarbonyloxybutyl group and a propylcarbonyloxymethyl group.

In general formula (3), examples of the alkyl groups represented by $R_{18}$ to $R_{21}$ include, but are not particularly limited to, a methyl group, an ethyl group, a propyl group, a butyl group, a pentyl group and a hexyl group.

In general formula (3), examples of the aryl groups represented by $R_{18}$ to $R_{21}$ include, but are not particularly limited to, a phenyl group, a 2-bromophenyl group, a 3-bromophenyl group, a 4-bromophenyl group, a 2-methoxyphenyl group, a 3-methoxyphenyl group, a 4-methoxyphenyl group, a 2-thiomethylphenyl group, a 3-thiomethylphenyl group, a 4-thiomethylphenyl group and a naphthyl group.

In general formula (3), examples of the alkoxy groups represented by $R_{18}$ to $R_{21}$ include, but are not particularly limited to, a methoxy group, an ethoxy group, a propoxy group and a butoxy group.

In general formula (3), examples of the halogen atoms represented by $R_{18}$ to $R_{21}$ include a fluorine atom, a chlorine atom, a bromine atom and an iodine atom.

In general formula (3), examples of the alkoxysulfonyl groups represented by $R_{18}$ to $R_{21}$ include, but are not particularly limited to, a methoxysulfonyl group and an ethoxysulfonyl group.

In general formula (3), examples of the N-alkylsulfamoyl groups represented by $R_{18}$ to $R_{21}$ include, but are not particularly limited to, a N-methylsulfamoyl group, a N-ethylsulfamoyl group, a N,N-dimethylsulfamoyl group and a N,N-diethylsulfamoyl group.

In general formula (3), examples of the alkyloxycarbonyl groups represented by $R_{18}$ to $R_{21}$ include, but are not particularly limited to, a methyloxycarbonyl group, an ethyloxycarbonyl group, a propyloxycarbonyl group and a butyloxycarbonyl group.

In general formula (3), examples of the N-alkylcarbamoyl groups represented by $R_{18}$ to $R_{21}$ include, but are not particularly limited to, a N-methylcarbamoyl group, a N-ethylcarbamoyl group, a N,N-dimethylcarbamoyl group and a N,N-diethylcarbamoyl group.

$R_{18}$ to $R_{21}$ each independently represent preferably a hydrogen atom, a halogen atom, a phenyl group or an alkoxy group, and more preferably a hydrogen atom or a phenyl group.

In general formula (3), examples of the alkyl groups represented by $R_{22}$ and $R_{23}$ include, but are not particularly limited to, a methyl group, an ethyl group, a propyl group and a butyl group.

In general formula (3), examples of the halogen atom represented by $R_{24}$ include a fluorine atom, a chlorine atom, a bromine atom and an iodine atom.

In general formula (3), examples of the alkyl group represented by $R_{25}$ include, but are not particularly limited to, a methyl group, an ethyl group, a propyl group, a butyl group, a pentyl group, a hexyl group and a 2-ethylhexyl group.

In general formula (3), examples of the aryl group represented by $R_{25}$ include, but are not particularly limited to, a phenyl group, a 2-bromophenyl group, a 3-bromophenyl group, a 4-bromophenyl group, a 2-methoxyphenyl group, a 3-methoxyphenyl group, a 4-methoxyphenyl group, a 2-methylthiophenyl group, a 3-methylthiophenyl group, a 4-methylthiophenyl group and a naphthyl group. Alternatively, groups represented by general formula (6) are mentioned. In general formula (6), reference symbol * represents a binding site.

General Formula (6)

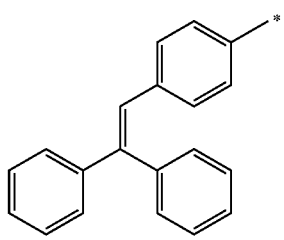

-continued

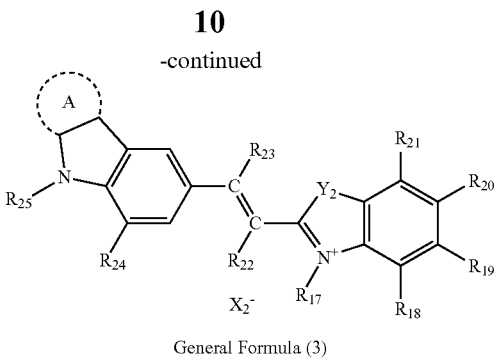

General Formula (3)

In general formula (3), examples of the aralkyl group represented by $R_{25}$ include, but are not particularly limited to, a benzyl group and a phenethyl group.

In general formula (3), examples of the anionic group represented by $X_2^-$ include, but are not particularly limited to, a chloride ion, a bromide ion, an iodide ion, a sulfate ion, a nitrate ion and a methanesulfonate ion.

In general formula (3), examples of the alkyl group of the nitrogen atom binding to an alkyl group represented by $Y_2$ include, but are not particularly limited to, a methyl group, an ethyl group, a propyl group and a butyl group.

In general formula (3), examples of the alkyl groups represented by $R_{26}$ and $R_{27}$ in $Y_2$ include, but are not particularly limited to, a methyl group, an ethyl group, a propyl group, a butyl group, a pentyl group, a hexyl group and a 2-ethylhexyl group. $R_{26}$ and $R_{27}$ are favorably the same substituents.

In general formula (3), examples of the aliphatic ring formed by binding $R_{26}$ and $R_{27}$ together in $Y_2$, include, but are not particularly limited to, a cyclohexane ring and a cyclopentane ring.

Compounds represented by general formula (3) in the present invention can be easily synthesized in the same manner as in known methods (for example, NPLs 3 to 5).

Now, an example of a synthesis scheme of the present invention will be shown below; however, the synthesis scheme is not limited to this.

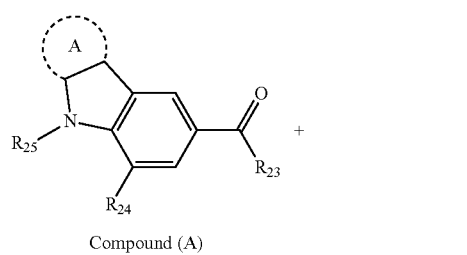

Compound (A)

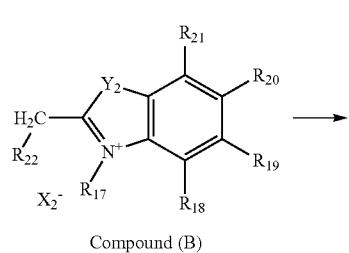

Compound (B)

In general formula (3), compound (A) and compound (B) above, $R_{17}$ to $R_{25}$, $X_2^-$, $Y_2$ and A are the same as defined in $R_{17}$ to $R_{25}$, $X_2^-$, $Y_2$ and A in general formula (3).

More specifically, a compound (A) is coupled with a compound (B) to obtain a compound represented by general formula (3). The coupling method is not particularly limited to; however, for example, the method shown below is specifically mentioned as an embodiment.

The use amount of compound (B) in the coupling step relative to compound (A) (1 mole) is 0.1 to 10 times by mole, preferably 0.5 to 3 times by mole, and more preferably 0.8 to 2 times by mole.

The coupling step can be performed in the absence of a solvent; however, it is favorably performed in the presence of a solvent. The solvent is not particularly limited as long as it is not involved in a reaction. Examples of the solvent include ester solvents such as methyl acetate, ethyl acetate, isopropyl acetate and butyl acetate; nitrile solvents such as acetonitrile, propionitrile and benzonitrile; aromatic solvents such as benzene, toluene, xylene, ethylbenzene, chlorobenzene and mesitylene; ether solvents such as diisopropyl ether, methyl-tert-butyl ether and tetrahydrofuran; alcohol solvents such as methanol, ethanol, n-propyl alcohol, iso-propyl alcohol, butyl alcohol and diethylene glycol; ketone solvents such as acetone and methylethyl ketone; dimethylformamide (DMF), dimethylsulfoxide (DMSO), water and acetic acid. Preferably, alcohol solvents such as methanol, ethanol, n-propyl alcohol, iso-propyl alcohol, butyl alcohol and diethylene glycol, water and acetic acid, and more preferably e.g., ethanol, iso-propyl alcohol and diethylene glycol and acetic acid are mentioned. Furthermore, two or more types of solvents can be used in combination and the mixing ratio of solvents used in combination can be determined at discretion.

The use amount of reaction solvent in the coupling step relative to compound (A) falls within the range of 0.1 to 1000 times by weight, preferably 0.5 to 500 times by weight, and more preferably 1.0 to 150 times by weight.

The reaction temperature in the coupling step falls within the range of $-80$ to $250°$ C., preferably $-20$ to $200°$ C., and more preferably $-5$ to $150°$ C. The reaction is generally completed within 24 hours.

In the coupling step, if an acid or a base is added as necessary, the reaction swiftly proceeds. The acid to be used is not particularly limited. Examples of the acid include inorganic acids such as hydrochloric acid, sulfuric acid and phosphoric acid; organic acids such as p-toluenesulfonic acid, formic acid, acetic acid, propionic acid, trifluoroacetic acid and acetic anhydride; strongly acidic ion exchange resins such as Amberlite (Rohm and Haas) and Amberlyst (Rohm and Haas); and inorganic acid salts such as ammonium formate and ammonium acetate. More preferably, an inorganic acid salt such as ammonium formate or ammonium acetate, and more preferably ammonium acetate is mentioned. The use amount of acid relative to compound (A) (1 mole) is 0.001 to 50 times by mole, preferably 0.01 to 10 times by mole, and more preferably 0.1 to 5 times by mole.

Specific examples of the base to be used in the coupling step include metal alkoxides such as potassium tert-butoxide, sodium tert-butoxide, sodium methoxide and sodium ethoxide; organic bases such as piperidine, pyridine, 2-methylpyridine, dimethylaminopyridine, diethylamine, triethylamine, isopropylethylamine, sodium acetate, potassium acetate, 1,8-diazabicyclo[5,4,0] undec-7-ene (hereinafter, simply referred to as DBU) and ammonium acetate; organic bases such as N-butyllithium and tert-magnesium chloride; and inorganic bases such as sodium borohydride, metallic sodium, sodium hydride and sodium carbonate. Preferably, potassium tert-butoxide, sodium methoxide, sodium ethoxide, piperidine, dimethylaminopyridine, sodium acetate and ammonium acetate; and more preferably sodium methoxide, piperidine, sodium acetate and ammonium acetate are mentioned. The use amount of base as mentioned above relative to compound (A) (1 mole) is 0.1 to 20 times by mole, preferably 0.5 to 8 times by mole, and more preferably 1.0 to 4 times by mole.

After completion of the reaction, a reaction product is diluted with water or precipitated with an acid such as hydrochloric acid to obtain a compound represented by general formula (3).

To the obtained compound, isolation/purification methods generally used for organic compounds can be applied. For example, a reaction solution is acidified with an acid such as hydrochloric acid to precipitate a solid substance. The solid substrate is separated by filtration, neutralized with e.g., sodium hydroxide and concentrated to obtain a crude product. The crude product is further purified by e.g., recrystallization using e.g., acetone or methanol, or a column using silica gel. The crude product can be highly purified by employing these methods alone or in combination with two or more.

Compound represented by general formula (4) As a preferable compound of the present invention, a compound represented by general formula (4) can be mentioned.

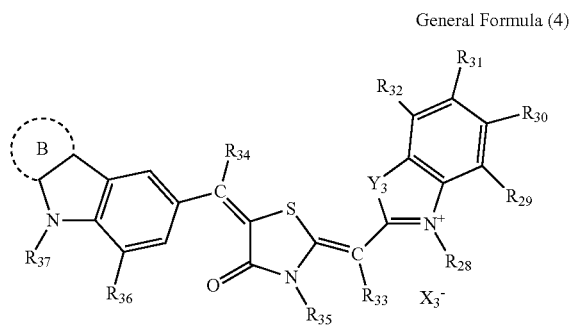

General Formula (4)

In general formula (4), $R_{28}$ each independently represents an alkyl group, a carboxylalkyl group, an alkoxycarbonylalkyl group or an alkylcarbonyloxyalkyl group; and $R_{29}$ to $R_{32}$ each independently represent a hydrogen atom, an alkyl group, an aryl group, an alkoxy group, a halogen atom, an alkoxysulfonyl group, a N-alkylsulfamoyl group, an alkyloxycarbonyl group or a N-alkylcarbamoyl group. $R_{33}$ and $R_{34}$ each independently represent a hydrogen atom, an alkyl group or a phenyl group; $R_{35}$ represents an alkyl group, a carboxylalkyl group, an alkoxycarbonylalkylgroup or an alkylcarbonyloxyalkyl group; $R_{36}$ represents a hydrogen atom or a halogen atom; and $R_{37}$ represents an alkyl group, an aryl group or an aralkyl group. $X_3^-$ represents an anionic group.

$Y_3$ represents an oxygen atom, a sulfur atom, a nitrogen atom binding to an alkyl group or —C($R_{38}$) ($R_{39}$)— where $R_{38}$ and $R_{39}$ each independently represent an alkyl group. $R_{38}$ and $R_{39}$ may bind together to form an aliphatic ring.

Reference symbol B represents a cyclopentane ring or a benzene ring.

In general formula (4), examples of the alkyl group represented by $R_{28}$ include, but are not particularly limited to, a methyl group, an ethyl group, a propyl group, a butyl group, a pentyl group and a hexyl group.

In general formula (4), examples of the carboxylalkyl group represented by $R_{28}$ include, but are not particularly limited to, a carboxylmethyl group, a carboxylethyl group and a carboxylpropyl group.

In general formula (4), examples of the alkoxycarbonylalkyl group represented by $R_{28}$ include, but are not particularly limited to, a methoxycarbonylmethyl group, a methoxycarbonylethyl group, an ethoxycarbonylethyl group, a butoxycarbonylethyl group and a methoxycarbonylpropyl group; and Examples of the alkylcarbonyloxyalkyl group include, but are not particularly limited to, a methylcarbonyloxymethyl group, an ethylcarbonyloxymethyl group, an ethylcarbonyloxyethyl group, an ethylcarbonyloxybutyl group and a propylcarbonyloxymethyl group.

In general formula (4), examples of the alkyl groups represented by $R_{29}$ to $R_{32}$ include, but are not particularly limited to, a methyl group, an ethyl group, a propyl group, a butyl group, a pentyl group and a hexyl group.

In general formula (4), examples of the aryl groups represented by $R_{29}$ to $R_{32}$ include, but are not particularly limited to, a phenyl group, a 2-bromophenyl group, a 3-bromophenyl group, a 4-bromophenyl group, a 2-methoxyphenyl group, a 3-methoxyphenyl group, a 4-methoxyphenyl group, a 2-thiomethylphenyl group, a 3-thiomethylphenyl group, a 4-thiomethylphenyl group and a naphthyl group.

In general formula (4), examples of the alkoxy groups represented by $R_{29}$ to $R_{32}$ include, but are not particularly limited to, a methoxy group, an ethoxy group, a propoxy group and a butoxy group.

In general formula (4), examples of the halogen atoms represented by $R_{29}$ to $R_{32}$ include a fluorine atom, a chlorine atom, a bromine atom and an iodine atom.

In general formula (4), examples of the alkoxysulfonyl groups represented by $R_{29}$ to $R_{32}$ include, but are not particularly limited to, a methoxysulfonyl group and an ethoxysulfonyl group.

In general formula (4), examples of the N-alkylsulfamoyl groups represented by $R_{29}$ to $R_{32}$ include, but are not particularly limited to, a N-methylsulfamoyl group, a N-ethylsulfamoyl group, a N,N-dimethylsulfamoyl group and a N,N-ethylsulfamoyl group.

In general formula (4), examples of the alkyloxycarbonyl groups represented by $R_{29}$ to $R_{32}$ include, but are not particularly limited to, a methyloxycarbonyl group, an ethyloxycarbonyl group, a propyloxycarbonyl group and a butyloxycarbonyl group.

In general formula (4), examples of the N-alkylcarbamoyl groups represented by $R_{29}$ to $R_{32}$ include, but are not particularly limited to, a N-methylcarbamoyl group, a N-ethylcarbamoyl group, a N,N-dimethylcarbamoyl group and a N,N-diethylcarbamoyl group.

$R_{29}$ to $R_{32}$ each independently represent preferably a hydrogen atom, a halogen atom, a phenyl group or an alkoxy group, and more preferably a hydrogen atom or a phenyl group.

In general formula (4), examples of the alkyl groups represented by $R_{33}$ and $R_{34}$ include, but are not particularly limited to, a methyl group, an ethyl group, a propyl group and a butyl group.

In general formula (4), examples of the alkyl group represented by $R_{35}$ include, but are not particularly limited to, a methyl group, an ethyl group, a propyl group, a butyl group, a pentyl group and a hexyl group.

In general formula (4), examples of the carboxylalkyl group represented by $R_{35}$ include, but are not particularly limited to, a carboxylmethyl group, a carboxylethyl group and a carboxylpropyl group.

In general formula (4), examples of the alkoxycarbonylalkyl group represented by $R_{35}$ include, but are not particularly limited to, a methoxycarbonylmethyl group, a methoxycarbonylethyl group, an ethoxycarbonylethyl group, a butoxycarbonylethyl group and a methoxycarbonylpropyl group; and Examples of the alkylcarbonyloxyalkyl group include, but are not particularly limited to, a methylcarbonyloxymethyl group, an ethylcarbonyloxymethyl group, an ethylcarbonyloxyethyl group, an ethylcarbonyloxybutyl group and a propylcarbonyloxymethyl group.

In general formula (4), examples of the halogen atom represented by $R_{36}$ include a fluorine atom, a chlorine atom, a bromine atom and an iodine atom.

In general formula (4), examples of the alkyl group represented by $R_{37}$ include, but are not particularly limited to, a methyl group, an ethyl group, a propyl group, a butyl group, a pentyl group, a hexyl group and a 2-ethylhexyl group.

In general formula (4), examples of the aryl group represented by $R_{37}$ include, but are not particularly limited to, a phenyl group, a 2-bromophenyl group, a 3-bromophenyl group, a 4-bromophenyl group, a 2-methoxyphenyl group, a 3-methoxyphenyl group, a 4-methoxyphenyl group, a 2-methylthiophenyl group, a 3-methylthiophenyl group, a 4-methylthiophenyl group and a naphthyl group. Alternatively, groups represented by general formula (6) are mentioned. In general formula (6), reference symbol * represents a binding site.

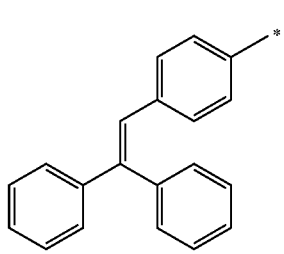

General Formula (6)

In general formula (4), examples of the aralkyl group represented by $R_{37}$ include, but are not particularly limited to, a benzyl group and a phenethyl group.

In general formula (4), examples of the anionic group represented by $X_3^-$ include, but are not particularly limited to, a chloride ion, a bromide ion, an iodide ion, a sulfate ion, a nitrate ion and a methanesulfonate ion.

In general formula (4), examples of the alkyl group of the nitrogen atom binding to an alkyl group represented by $Y_3$ include, but are not particularly limited to, a methyl group, an ethyl group, a propyl group and a butyl group.

In general formula (4), examples of the alkyl groups represented by $R_{38}$ and $R_{39}$ in $Y_3$ include, but are not particularly limited to, a methyl group, an ethyl group, a propyl group, a butyl group, a pentyl group, a hexyl group and a 2-ethylhexyl group. $R_{38}$ and $R_{39}$ are favorably the same substituents.

In general formula (4), examples of the aliphatic ring formed by binding $R_{38}$ and $R_{39}$ together in $Y_3$, include, but are not particularly limited to, a cyclohexane ring and a cyclopentane ring.

Compounds represented by general formula (4) in the present invention can be easily synthesized in the same manner as in known methods (for example, PTL 2).

Now, an example of a synthesis scheme of the present invention will be shown below; however, the synthesis scheme is not limited to this.

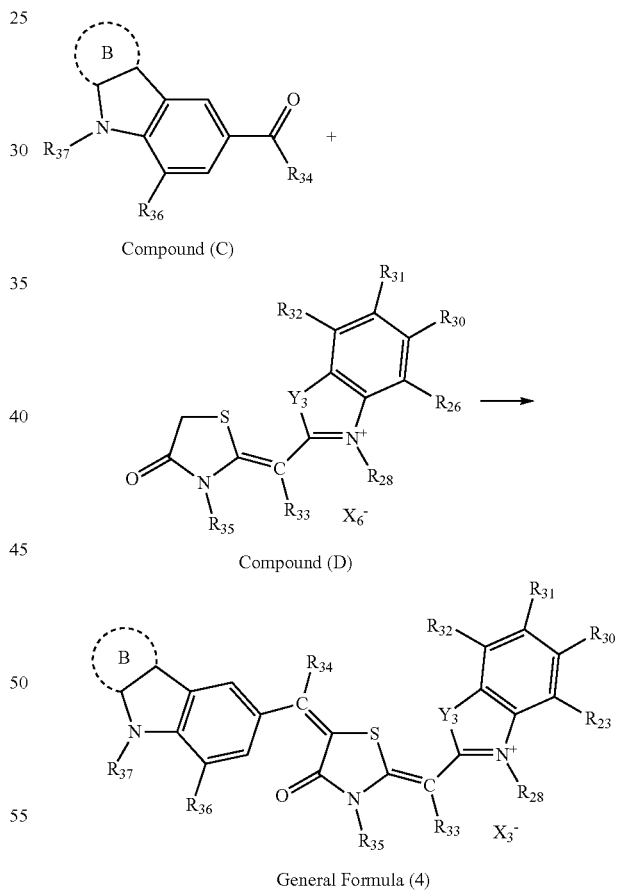

In general formula (4), compound (C) and compound (D) above, $R_{28}$ to $R_{36}$, $X_3^-$, $Y_3$ and B are the same as defined in $R_{28}$ to $R_{36}$, $X_3^-$, $Y_3$ and B in general formula (4).

More specifically, a compound (C) is coupled with a compound (D) to obtain a compound represented by general formula (4). The coupling method is not particularly limited to; however, for example, the method shown below is specifically mentioned as an embodiment.

The use amount of compound (D) in the coupling step relative to compound (C) (1 mole) is 0.1 to 10 times by mole, preferably 0.5 to 3 times by mole, and more preferably 0.8 to 2 times by mole.

The coupling step can be performed in the absence of a solvent; however, it is favorably performed in the presence of a solvent. The solvent is not particularly limited as long as it is not involved in a reaction. Examples of the solvent include ester solvents such as methyl acetate, ethyl acetate, isopropyl acetate and butyl acetate; nitrile solvents such as acetonitrile, propionitrile and benzonitrile; aromatic solvents such as benzene, toluene, xylene, ethylbenzene, chlorobenzene and mesitylene; ether solvents such as diisopropyl ether, methyl-tert-butyl ether and tetrahydrofuran; alcohol solvents such as methanol, ethanol, n-propyl alcohol, iso-propyl alcohol, butyl alcohol and diethylene glycol; ketone solvents such as acetone and methylethyl ketone; dimethylformamide (DMF), dimethylsulfoxide (DMSO), water and acetic acid. Preferably, alcohol solvents such as methanol, ethanol, n-propyl alcohol, iso-propyl alcohol, butyl alcohol and diethylene glycol, water and acetic acid, and more preferably e.g., ethanol, iso-propyl alcohol and diethylene glycol and acetic acid are mentioned. Furthermore, two or more types of solvents can be used in combination and the mixing ratio of solvents used in combination can be determined at discretion.

The use amount of reaction solvent in the coupling step relative to compound (C) falls within the range of 0.1 to 1000 times by weight, preferably 0.5 to 500 times by weight, and more preferably 1.0 to 150 times by weight.

The reaction temperature in the coupling step falls within the range of −80 to 250° C., preferably −20 to 200° C., and more preferably −5 to 150° C. The reaction is generally completed within 24 hours.

In the coupling step, if an acid or a base is added as necessary, the reaction swiftly proceeds. The acid to be used is not particularly limited. Examples of the acid include inorganic acids such as hydrochloric acid, sulfuric acid and phosphoric acid; organic acids such as p-toluenesulfonic acid, formic acid, acetic acid, propionic acid, trifluoroacetic acid and acetic anhydride; strongly acidic ion exchange resins such as Amberlite (Rohm and Haas) and Amberlyst (Rohm and Haas); and inorganic acid salts such as ammonium formate and ammonium acetate. More preferably, an inorganic acid salt such as ammonium formate or ammonium acetate, and more preferably ammonium acetate is mentioned. The use amount of acid relative to compound (C) (1 mole) is 0.001 to 50 times by mole, preferably 0.01 to 10 times by mole, and more preferably 0.1 to 5 times by mole.

Specific examples of the base to be used in the coupling step include metal alkoxides such as potassium tert-butoxide, sodium tert-butoxide, sodium methoxide and sodium ethoxide; organic bases such as piperidine, pyridine, 2-methylpyridine, dimethylaminopyridine, diethylamine, triethylamine, isopropylethylamine, sodium acetate, potassium acetate, 1,8-diazabicyclo[5,4,0] undec-7-ene (hereinafter, simply referred to as DBU) and ammonium acetate; organic bases such as N-butyllithium and tert-magnesium chloride; and inorganic bases such as sodium borohydride, metallic sodium, sodium hydride and sodium carbonate. Preferably, potassium tert-butoxide, sodium methoxide, sodium ethoxide, piperidine, dimethylaminopyridine, sodium acetate and ammonium acetate; and more preferably sodium methoxide, piperidine, sodium acetate and ammonium acetate are mentioned. The use amount of base as mentioned above relative to compound (C) (1 mole) is 0.1 to 20 times by mole, preferably 0.5 to 8 times by mole, and more preferably 1.0 to 4 times by mole.

After completion of the reaction, a reaction product is diluted with water or precipitated with an acid such as hydrochloric acid to obtain a compound represented by general formula (4).

To the obtained compound, isolation/purification methods generally used for organic compounds can be applied. For example, a reaction solution is acidified with an acid such as hydrochloric acid to precipitate a solid substance. The solid substrate is separated by filtration, neutralized with e.g., sodium hydroxide and concentrated to obtain a crude product. Furthermore, the crude product is purified by e.g., recrystallization using e.g., acetone or methanol, or a column using silica gel. The crude product can be highly purified by employing these methods alone or in combination with two or more.

Compound represented by general formula (5) As a preferable compound of the present invention, a compound represented by general formula (5) can be mentioned.

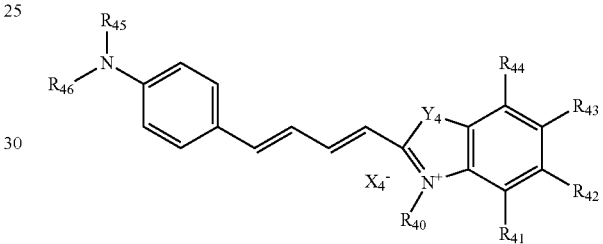

General Formula (5)

In general formula (5), $R_{40}$ each independently represents an alkyl group, a carboxylalkyl group, an alkoxycarbonylalkyl group or an alkylcarbonyloxyalkyl group; and $R_{41}$ to $R_{44}$ each independently represent a hydrogen atom, an alkyl group, an aryl group, an alkoxy group, a halogen atom, an alkoxysulfonyl group, a N-alkylsulfamoyl group, an alkyloxycarbonyl group or a N-alkylcarbamoyl group. $R_{45}$ and $R_{46}$ each independently represent, an alkyl group or an aryl group.

$Y_4$ represents an oxygen atom, a sulfur atom, a nitrogen atom binding to an alkyl group or —C($R_{47}$) ($R_{48}$)— where $R_{47}$ and $R_{48}$ each independently represent an alkyl group. $R_{47}$ and $R_{48}$ may bind together to form an aliphatic ring.

In general formula (5), examples of the alkyl group represented by $R_{40}$ include, but are not particularly limited to, a methyl group, an ethyl group, a propyl group, a butyl group, a pentyl group and a hexyl group.

In general formula (5), examples of the carboxylalkyl group represented by $R_{40}$ include, but are not particularly limited to, a carboxylmethyl group, a carboxylethyl group and a carboxylpropyl group.

In general formula (5), examples of the alkoxycarbonylalkyl group represented by $R_{40}$ include, but are not particularly limited to, a methoxycarbonylmethyl group, a methoxycarbonylethyl group, an ethoxycarbonylethyl group, a butoxycarbonylethyl group and a methoxycarbonylpropyl group; and Examples of the alkylcarbonyloxyalkyl group include, but are not particularly limited to, a methylcarbonyloxymethyl group, an ethylcarbonyloxymethyl group, an ethylcarbonyloxyethyl group, an ethylcarbonyloxybutyl group and a propylcarbonyloxymethyl group.

In general formula (5), examples of the alkyl groups represented by $R_{41}$ to $R_{44}$ include, but are not particularly limited to, a methyl group, an ethyl group, a propyl group, a butyl group, a pentyl group and a hexyl group.

In general formula (5), examples of the aryl groups represented by $R_{41}$ to $R_{44}$ include, but are not particularly limited to, a phenyl group, a 2-bromophenyl group, a 3-bromophenyl group, a 4-bromophenyl group, a 2-methoxyphenyl group, a 3-methoxyphenyl group, a 4-methoxyphenyl group, a 2-thiomethylphenyl group, a 3-thiomethylphenyl group, a 4-thiomethylphenyl group and a naphthyl group.

In general formula (5), examples of the alkoxy groups represented by $R_{41}$ to $R_{44}$ include, but are not particularly limited to, a methoxy group, an ethoxy group, a propoxy group and a butoxy group.

In general formula (5), examples of the halogen atoms represented by $R_{41}$ to $R_{44}$ include a fluorine atom, a chlorine atom, a bromine atom and an iodine atom.

In general formula (5), examples of the alkoxysulfonyl groups represented by $R_{41}$ to $R_{44}$ include, but are not particularly limited to, a methoxysulfonyl group and an ethoxysulfonyl group.

In general formula (5), examples of the N-alkylsulfamoyl groups represented by $R_{41}$ to $R_{44}$ include, but are not particularly limited to, a N-methylsulfamoyl group, a N-ethylsulfamoyl group, a N,N-dimethylsulfamoyl group and a N,N-ethylsulfamoyl group.

In general formula (5), examples of the alkyloxycarbonyl groups represented by $R_{41}$ to $R_{44}$ include, but are not particularly limited to, a methyloxycarbonyl group, an ethyloxycarbonyl group, a propyloxycarbonyl group and a butyloxycarbonyl group.

In general formula (5), examples of the N-alkylcarbamoyl groups represented by $R_{41}$ to $R_{44}$ include, but are not particularly limited to, a N-methylcarbamoyl group, a N-ethylcarbamoyl group, a N,N-dimethylcarbamoyl group and a N,N-diethylcarbamoyl group.

$R_{41}$ to $R_{44}$ each independently represent preferably a hydrogen atom, a halogen atom, a phenyl group or an alkoxy group, and more preferably a hydrogen atom or a phenyl group.

In general formula (5), examples of the alkyl groups represented by $R_{45}$ and $R_{46}$ include, but are not particularly limited to, a methyl group, an ethyl group, a propyl group, a butyl group, a pentyl group and a hexyl group and a 2-ethylhexyl group.

In general formula (5), examples of the aryl groups represented by $R_{45}$ and $R_{46}$ include, but are not particularly limited to, a phenyl group, a 2-bromophenyl group, a 3-bromophenyl group, a 4-bromophenyl group, a 2-methoxyphenyl group, a 3-methoxyphenyl group, a 4-methoxyphenyl group, a 2-thiomethylphenyl group, a 3-thiomethylphenyl group, a 4-thiomethylphenyl group and a naphthyl group.

In general formula (5), examples of the anionic group represented by $X_4^-$ include, but are not particularly limited to, a chloride ion, a bromide ion, an iodide ion, a sulfate ion, a nitrate ion and a methanesulfonate ion.

In general formula (5), examples of the alkyl group of the nitrogen atom binding to an alkyl group represented by $Y_4$ include, but are not particularly limited to, a methyl group, an ethyl group, a propyl group and a butyl group.

In general formula (5), examples of the alkyl groups represented by $R_{47}$ and $R_{48}$ in $Y_4$ include, but are not particularly limited to, a methyl group, an ethyl group, a propyl group, a butyl group, a pentyl group, a hexyl group and a 2-ethylhexyl group. $R_{47}$ and $R_{48}$ are favorably the same substituents.

In general formula (5), examples of the aliphatic ring formed by binding $R_{47}$ and $R_{48}$ together in $Y_4$, include, but are not particularly limited to, a cyclohexane ring and a cyclopentane ring.

Compounds represented by general formula (5) in the present invention can be easily synthesized in the same manner as in known methods (for example, NPL 6). Now, an example of a synthesis scheme of the present invention will be shown below; however, the synthesis scheme is not limited to this.

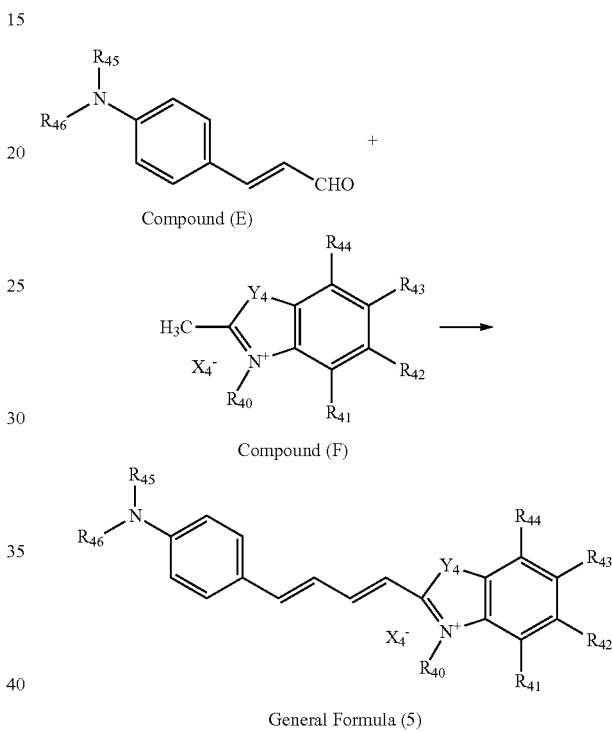

Compound (E)

Compound (F)

General Formula (5)

In general formula (5), compound (E) and compound (F) above, $R_{40}$ to $R_{46}$ and $X_4^-$, $Y_4$ are the same as defined in $R_{40}$ to $R_{46}$ and $X_4^-$, $Y_4$ in general formula (5).

More specifically, a compound (E) is coupled with a compound (F) to obtain a compound represented by general formula (5). The coupling method is not particularly limited to; however, for example, the method shown below is specifically mentioned as an embodiment.

The use amount of compound (F) in the coupling step relative to compound (E) (1 mole) is 0.1 to 10 times by mole, preferably 0.5 to 3 times by mole, and more preferably 0.8 to 2 times by mole.

The coupling step can be performed in the absence of a solvent; however, it is favorably performed in the presence of a solvent. The solvent is not particularly limited as long as it is not involved in a reaction. Examples of the solvent include ester solvents such as methyl acetate, ethyl acetate, isopropyl acetate and butyl acetate; nitrile solvents such as acetonitrile, propionitrile and benzonitrile; aromatic solvents such as benzene, toluene, xylene, ethylbenzene, chlorobenzene and mesitylene; ether solvents such as diisopropyl ether, methyl-tert-butyl ether and tetrahydrofuran; alcohol solvents such as methanol, ethanol, n-propyl alcohol, iso-propyl alcohol, butyl alcohol and diethylene glycol;

ketone solvents such as acetone and methylethyl ketone; dimethylformamide (DMF), dimethylsulfoxide (DMSO), water and acetic acid. Preferably, alcohol solvents such as methanol, ethanol, n-propyl alcohol, iso-propyl alcohol, butyl alcohol and diethylene glycol, water and acetic acid, and more preferably e.g., ethanol, iso-propyl alcohol and diethylene glycol and acetic acid are mentioned. Furthermore, two or more types of solvents can be used in combination and the mixing ratio of solvents used in combination can be determined at discretion.

The use amount of reaction solvent in the coupling step relative to compound (E) falls within the range of 0.1 to 1000 times by weight, preferably 0.5 to 500 times by weight, and more preferably 1.0 to 150 times by weight.

The reaction temperature in the coupling step falls within the range of −80 to 250° C., preferably −20 to 200° C., and more preferably −5 to 150° C. The reaction is generally completed within 24 hours.

In the coupling step, if an acid or a base is added as necessary, the reaction swiftly proceeds. The acid to be used is not particularly limited. Examples of the acid include inorganic acids such as hydrochloric acid, sulfuric acid and phosphoric acid; organic acids such as p-toluenesulfonic acid, formic acid, acetic acid, propionic acid, trifluoroacetic acid and acetic anhydride; strongly acidic ion exchange resins such as Amberlite (Rohm and Haas) and Amberlyst (Rohm and Haas); and inorganic acid salts such as ammonium formate and ammonium acetate. More preferably, an inorganic acid salt such as ammonium formate or ammonium acetate, and more preferably ammonium acetate is mentioned. The use amount of acid relative to compound (E) (1 mole) is 0.001 to 50 times by mole, preferably 0.01 to 10 times by mole, and more preferably 0.1 to 5 times by mole.

Specific examples of the base to be used in the coupling step include metal alkoxides such as potassium tert-butoxide, sodium tert-butoxide, sodium methoxide and sodium ethoxide; organic bases such as piperidine, pyridine, 2-methylpyridine, dimethylaminopyridine, diethylamine, triethylamine, isopropylethylamine, sodium acetate, potassium acetate, 1,8-diazabicyclo[5,4,0] undec-7-ene (hereinafter, simply referred to as DBU) and ammonium acetate; organic bases such as N-butyllithium and tert-butylmagnesium chloride; and inorganic bases such as sodium borohydride, metallic sodium, sodium hydride and sodium carbonate. Preferably, potassium tert-butoxide, sodium methoxide, sodium ethoxide, piperidine, dimethylaminopyridine, sodium acetate and ammonium acetate; and more preferably sodium methoxide, piperidine, sodium acetate and ammonium acetate are mentioned. The use amount of base as mentioned above relative to compound (E) (1 mole) is 0.1 to 20 times by mole, preferably 0.5 to 8 times by mole, and more preferably 1.0 to 4 times by mole.

After completion of the reaction, a reaction product is diluted with water or precipitated with an acid such as hydrochloric acid to obtain a compound represented by general formula (5).

To the obtained compound, isolation/purification methods generally used for organic compounds can be applied. For example, a reaction solution is acidified with an acid such as hydrochloric acid to precipitate a solid substance. The solid substrate is separated by filtration, neutralized with e.g., sodium hydroxide and concentrated to obtain a crude product. Furthermore, the crude product is purified by e.g., recrystallization using e.g., acetone or methanol, or a column using silica gel. The crude product can be highly purified by employing these methods alone or in combination with two or more.

Now, compounds (1) to (46) will be shown below as preferable examples of the compounds represented by general formulas (1) to (5) of the present invention; however, the compounds of the present invention are not limited to the following examples.

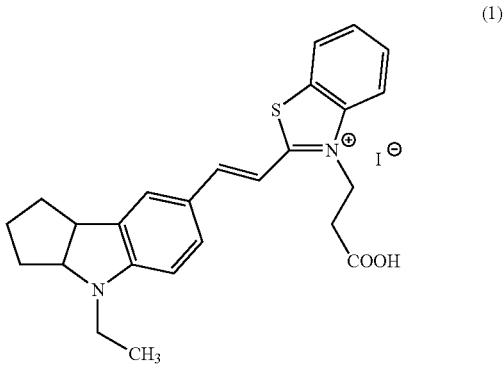

(1)

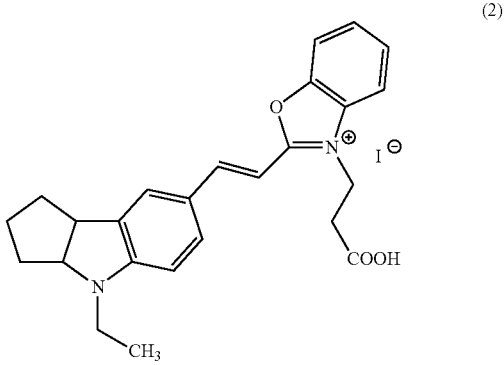

(2)

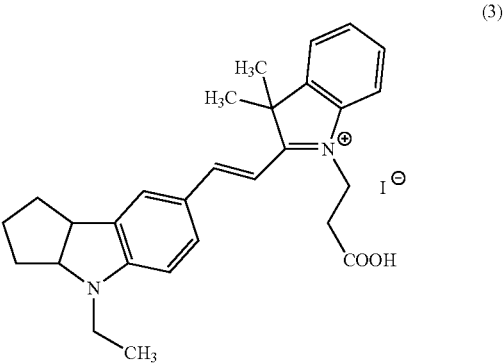

(3)

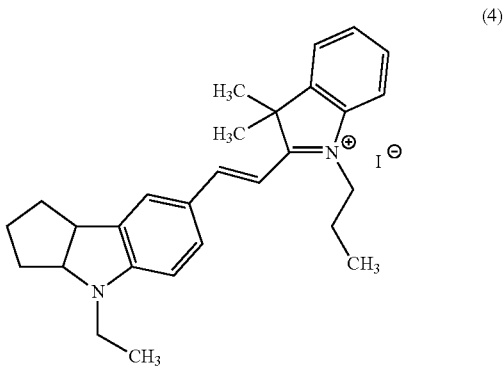

(4)

-continued
(5)
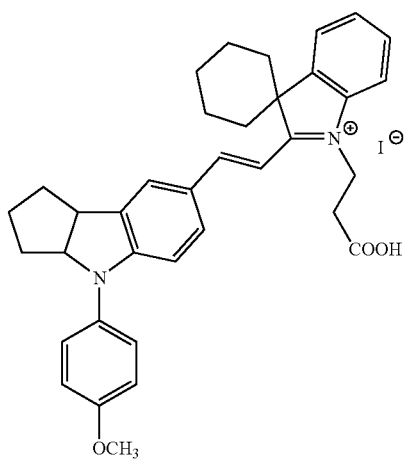
(6)
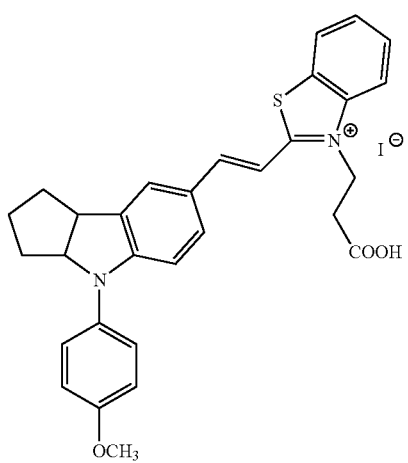
(7)
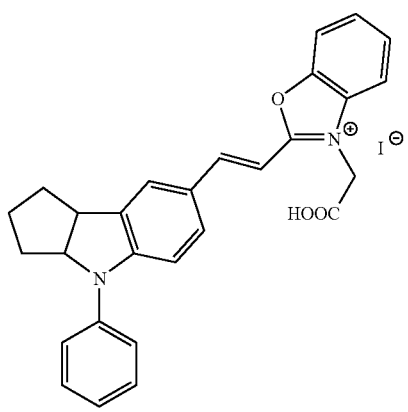
-continued
(8)
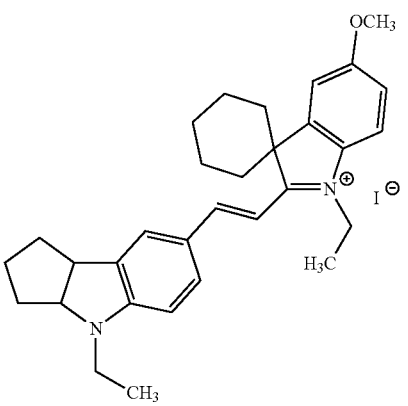
(9)
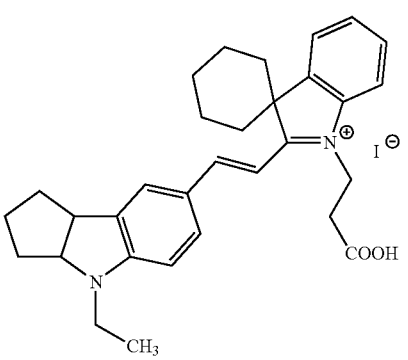
(10)
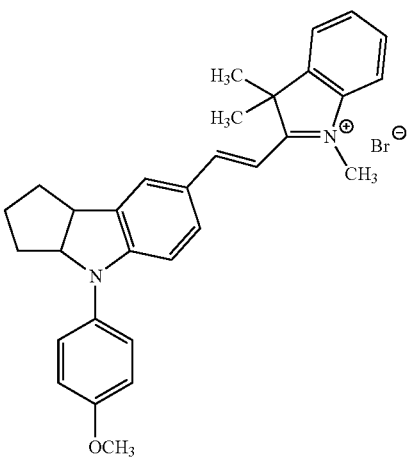
(11)

-continued
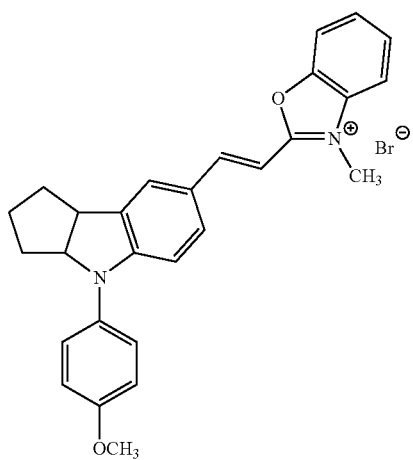
(12)
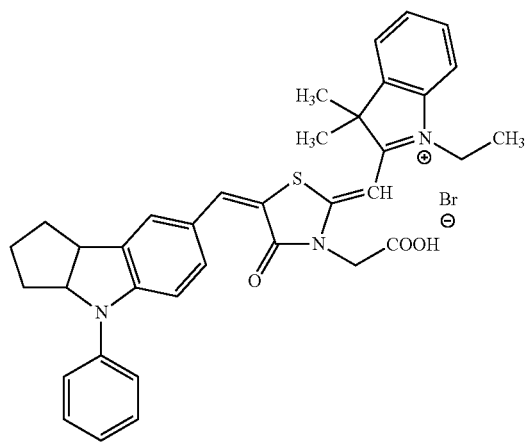
(15)
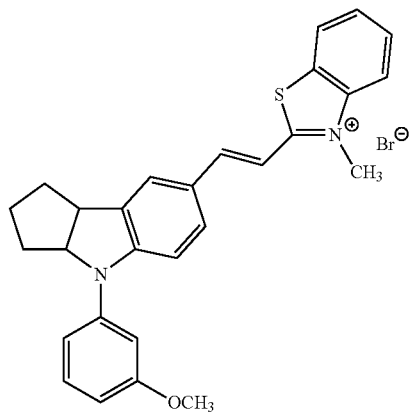
(13)
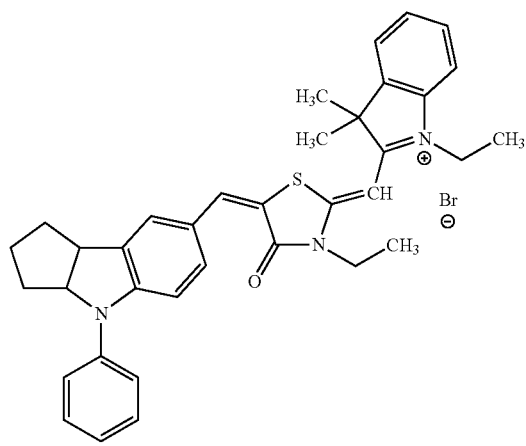
(16)
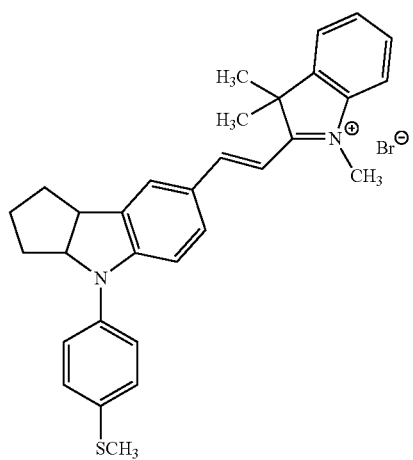
(14)
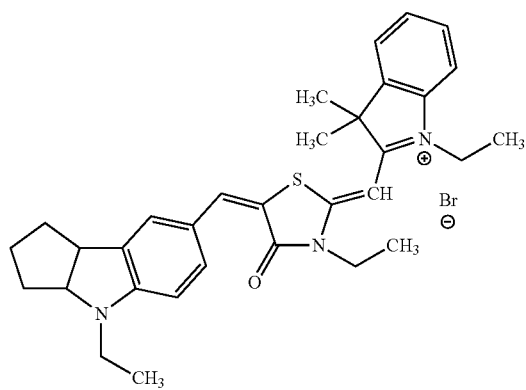
(17)

(18)
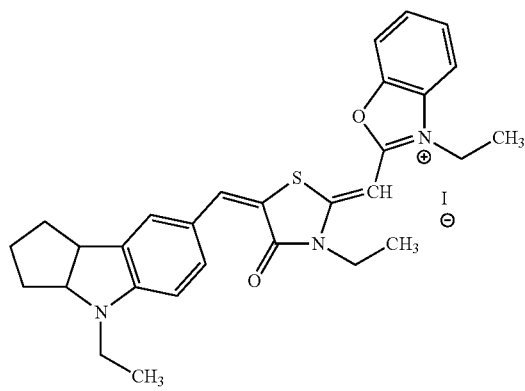
(19)
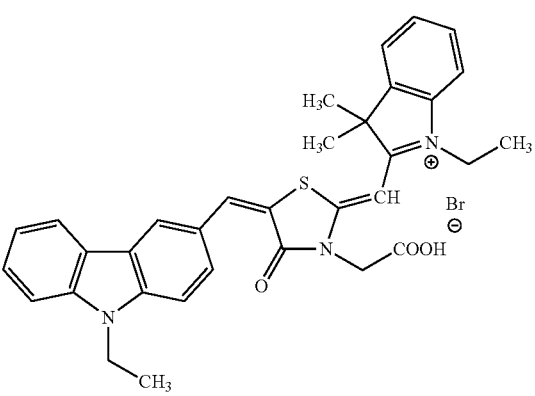
(20)
(21)
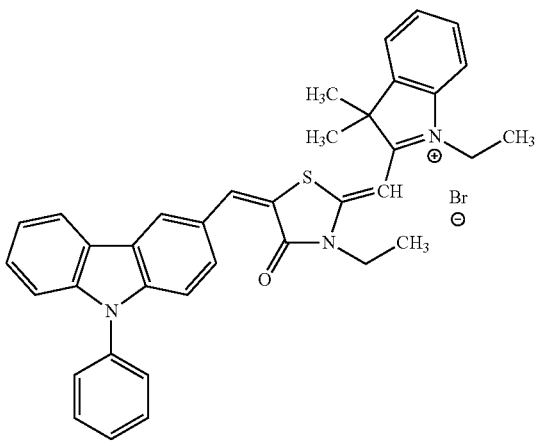
(22)
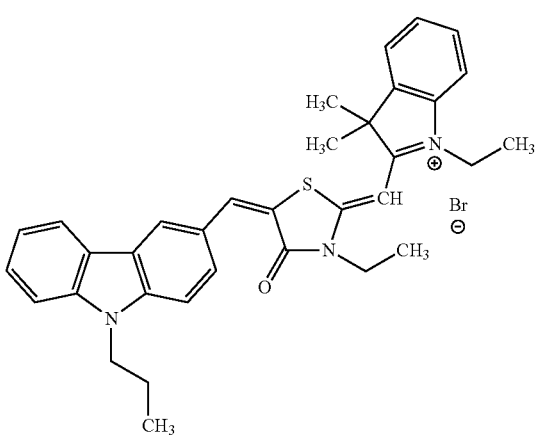
(23)
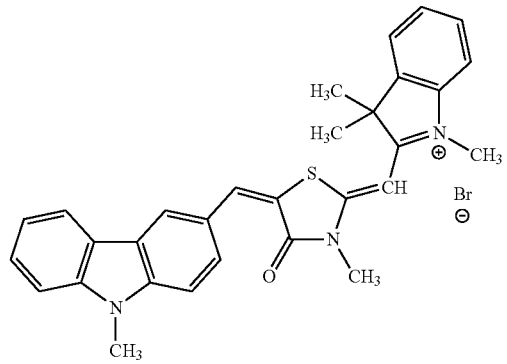
(24)
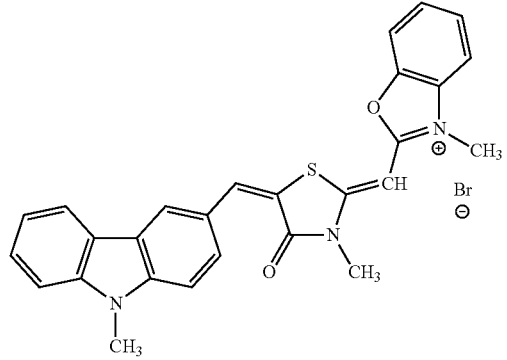

(25)
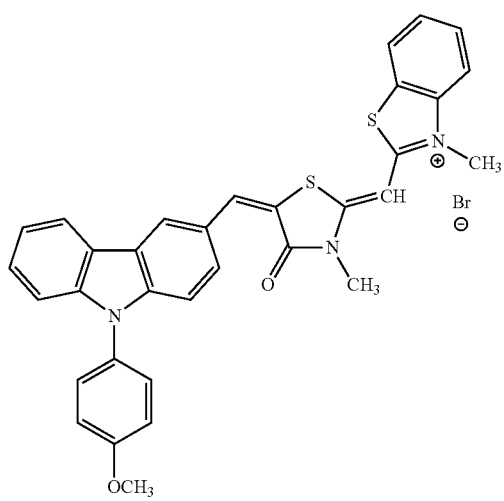
(26)
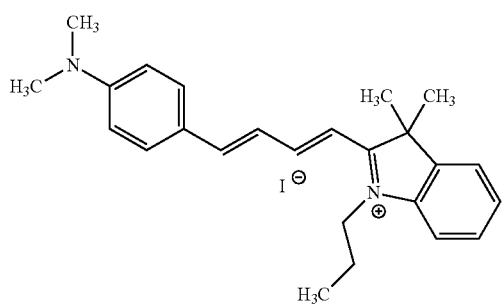
(27)
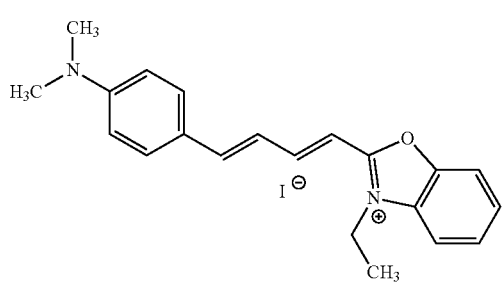
(28)
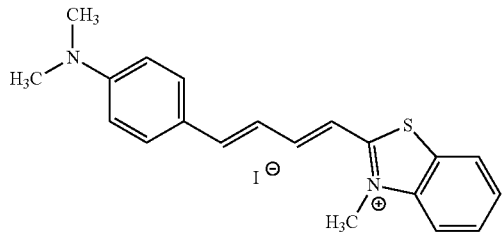
(29)
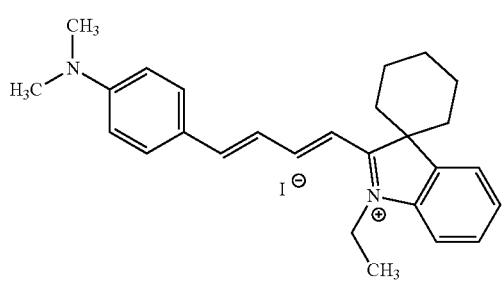
(30)
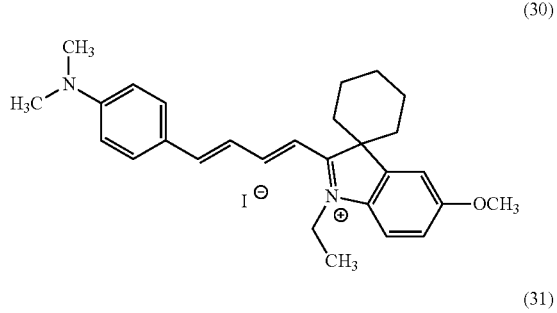
(31)
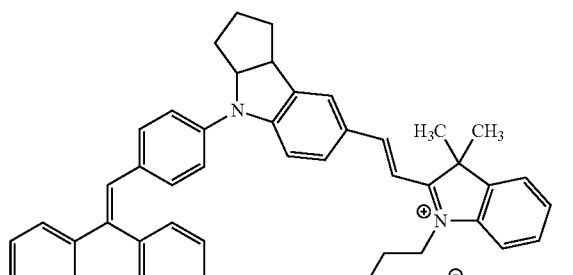
(32)
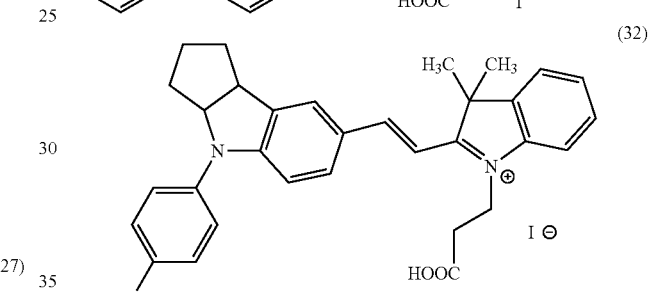
(33)
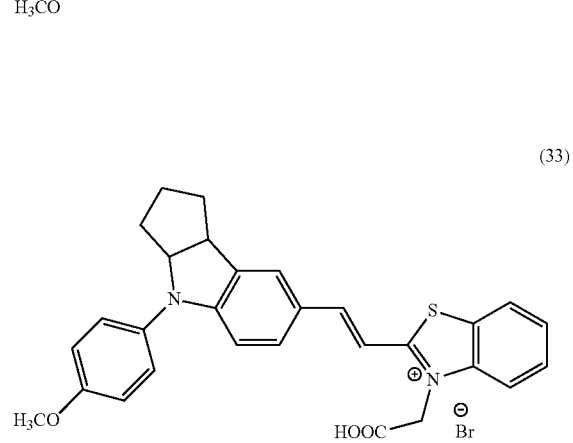
(34)
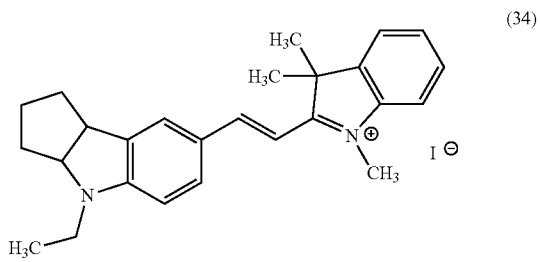

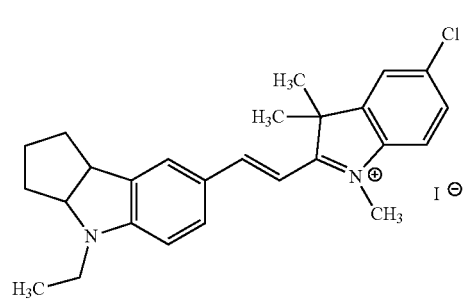
(35)
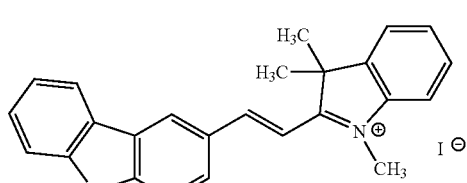
(36)
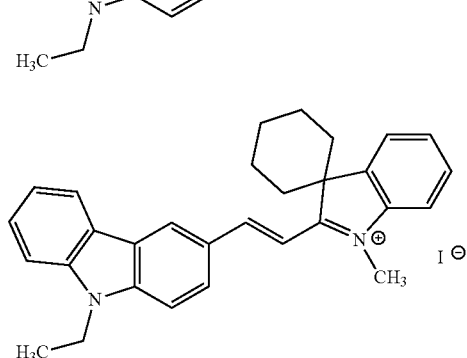
(37)
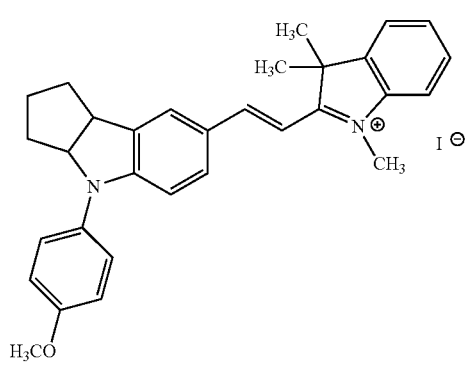
(38)
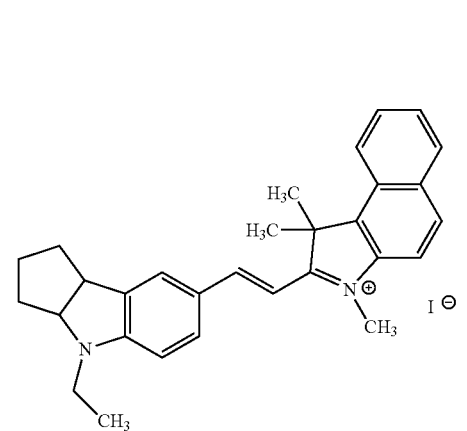
(39)
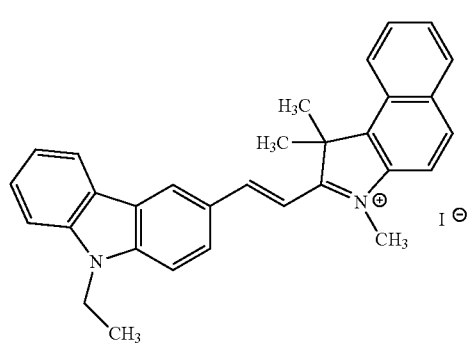
(40)
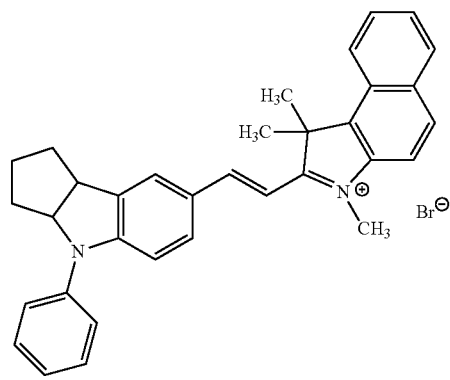
(41)
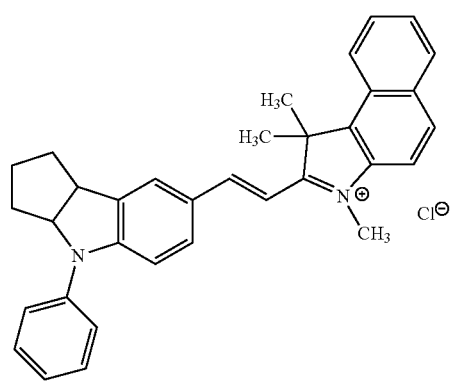
(42)
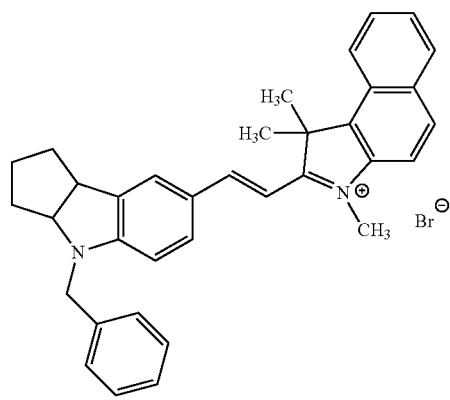
(43)

(44)

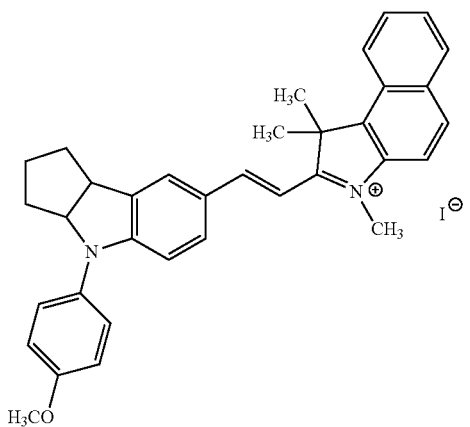

(45)

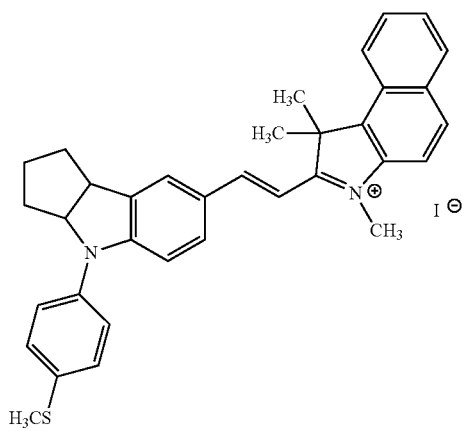

(46)

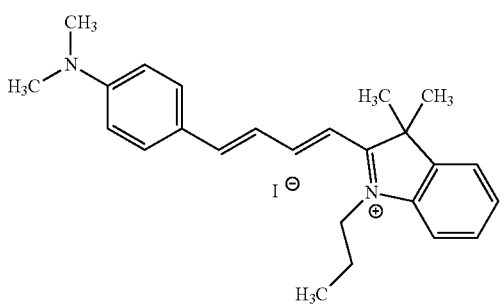

The compounds of the present invention are characterized by emitting light upon irradiation with excitation light of 350 to 800 nm in wavelength. The emission light, i.e., luminescence, referred to in the present invention can include fluorescence and phosphorescence.

The cancer cell inhibitory drug of the present invention is characterized in that growth suppression, cellular division suppression, metastasis suppression, functional inhibition and cytocidal action of cancer cells are mediated by taking a compound represented by general formula (1) of the present invention selectively into the cancer cells. At the same time, cancer cells can be detected and observed by measuring luminescence of the compound of the present invention.

The cancer cell inhibitory drugs of the present invention can be used alone or in combination of two or more types, and may be used in combination with a known anti-cancer drug(s).

In the present invention, a large effect is selectively exerted particularly on cancer stem cells among cancer cells.

Cancer Stem Cells

In the specification, the cancer stem cells refer to cancer cells having properties of the stem cells. The stem cells refer to cells having two functions, i.e., self-replication ability and pluripotency (ability to differentiate into various types of cells).

Applicable Cancer

The cancers to which the cancer cell inhibitory drugs of the present invention are applicable are not particularly limited. Examples of the cancers include breast cancer, brain tumor, stomach cancer, prostatic cancer, pancreatic cancer, lung cancer, large bowel cancer, small intestine cancer, colon cancer, rectal cancer, esophagus cancer, duodenal cancer, tongue cancer, pharyngeal cancer, liver cancer, endometrium cancer, uterine cervix cancer, renal cancer, bile duct cancer, ovarian cancer, bladder cancer, skin cancer, blood vessel cancer, salivary gland cancer, thyroid cancer, parathyroid gland cancer, nasal cavity cancer, paranasal sinus cancer, penile cancer, infant solid cancer, malignant lymphoma, malignant melanoma, retina sarcoma, testicular tumor, myeloma, sarcoma, blood vessel fibroma and leukemia. Preferably, e.g., pancreatic cancer, prostatic cancer and leukemia are mentioned. Particularly, applicable cancers may include cancer stem cells or cells originated from cancer stem cells.

Test Subject

Examples of the subject used in a test for checking whether a compound of the present invention suppresses a cancer or not include, but are not particularly limited to, vertebral animals including bony fish such as *Takifugu* (Japanese pufferfish), *Takifugu niphobles*, green spotted pufferfish (*Tetraodon nigroviridis*), killifish and zebra fish, amphibians such as Xenopus, birds such as fowl and quail, mammalians such as human, monkey, chimpanzee, calf, horse, pig, dog, cat, mouse, rat, guinea pig, and hamster and rabbit; small animals such as rat, mouse and hamster; and large animals such as goat, pig, dog, cat, calf and horse, monkey and chimpanzee. Favorably, e.g., mouse, rat, dog and cat are mentioned.

When a compound of the present invention is used as a medicinal drug, various types of dosage forms can be selected depending upon the administration route. Examples of dosage forms that can be used include liquid, syrup, fine granule, granule, tablet, capsule, pasting medicine and drug delivery system (DDS) such as liposome.

The administration method of a compound of the present invention is not limited and oral or parenteral administration may be used. Examples of the administration method that can be used include exposure to a living body (e.g., liquid); administration such as oral, intravascular (through e.g., a vein or an artery), peroral, sublingual, intrarectal, intraperitoneal, dermal, subcutaneous, intracutaneous, intravesical, tracheal (via bronchia), intraocular and intranasal administrations; and injection, spray and application into ear or the like.

A compound of the present invention, if necessary, may contain pharmacologically or pharmaceutically acceptable additives such as a moisturizer, a surface tension moderator, a thickener, a pH moderator, a pH buffer, a preservative, an antibacterial agent, a sweetening agent, a flavor, a solubilizer, a solubilizing agent, a coating agent and a binder.

The dose of the cancer cell inhibitory drug of the present invention is appropriately determined depending upon a purpose for therapy or prophylaxis, and conditions such as sexuality, age, weight of a test subject, an administration route, and degree of a disease.

Transplant Model Animal

Generally, it is difficult to monitor behavior of metastatic cancer by culturing cells. Thus, in the present invention, in order to monitor behavior of metastatic cancer, particularly, a transplant model animal can be used.

Examples of the cancer-cell transplant model animal applicable to the present invention include, but are not particularly limited to, vertebral animals including bony fish such as *Takifugu* (Japanese pufferfish), *Takifugu niphobles*, green spotted pufferfish (*Tetraodon nigroviridis*), killifish and zebra fish, amphibians such as Xenopus, birds such as fowl and quail, and mammalians such as human, monkey, chimpanzee, calf, horse, pig, dog, cat, mouse, rat, guinea pig, hamster and rabbit; small animals such as rat, mouse and hamster; and large animals such as goat, pig, dog, cat, calf and horse, monkey and chimpanzee. Favorably, e.g., mouse, rat, dog and cat are mentioned.

Of these, e.g., immunodeficiency mice and rats, are often generally used in an initial study. In this case, it is necessary to maintain an environment by use of e.g., a clean room in the period (usually, at least 3 to 6 months) during which the study is carried out. In addition, extraordinary labor cost for management during this period is required.

For the reason, among these biological samples, zebra fish is particularly preferably used in view of cost and speed (usually at least a week). Zebra fish has been recently and already recognized as a third model animal which comes next to mice and rats in the United States and the United Kingdom. It has been elucidated that, the entire genomic sequence of zebra fish has a 80% homology to that of a human and the number of genes of zebra fish is virtually the same as that of a human. Furthermore, development and structure of major organs/tissues are mutually quite resembled. Since a process from differentiation of a fertilized egg to formation of each part (organ such as heart, liver, kidney and digestive tube) can be observed through a transparent body, it is particularly preferable to use zebra fish (the inside of which can be observed non-invasively) for screening as a model animal.

Furthermore, zebra fish lay about 200 or more fertilized eggs per time. Since zebra fish having the same genetic background are obtained, zebra fish is advantageous for screening.

The method for administering a compound of the present invention is not particularly limited; however, a cancer cell inhibitory drug may be suspended in the form of a complex with an appropriate surfactant or in the form of an emulsion in breeding water. Alternatively, the cancer cell inhibitory drug may be mixed in feed or food and orally or parenterally (e.g., injection) administered.

Cancer Stem Cell Detection Probe

Since a compound of the present invention can selectively detect cancer stem cells, it can be favorably used as a cancer stem cell detection probe. More specifically, the present invention encompasses a cancer cell detection probe.

The ratio of the present invention particularly taken into cancer stem cells among the cancer cells is large. Thus, cancer stem cells can be selectively detected. Detection and confirmation of behavior of cancer stem cells by the present invention can be carried out all in vitro, ex vivo or in vivo.

A method for detecting cancer stem cells by use of a compound of the present invention, which is not particularly limited as long as it has no effect upon cancer stem cells, is a method for capturing state and change of a biological sample as an image. For example, visible light, near infrared light or infrared light is applied to cancer stem cells and an image is visually observed by e.g., a camera or CCD, namely, visible light observation, near infrared light observation and infrared light observation are mentioned.

Alternatively, observation by a laser microscope; fluorescence observation in which excitation light is applied to a biological sample from an excitation-light source and fluorescence emitted from the biological sample is observed by a fluorescent endoscope or the like; observation by a fluorescent microscope; observation by a fluorescent endoscope; observation by a cofocus fluorescence microscope; or observation by a multiphoton excitation fluorescence microscope is mentioned. Alternatively, narrow-band light observation; colight interference tomogram observation (OCT) or observation by a soft X ray microscope is mentioned. Particularly, fluorescence observation is favorable.

The wavelength of light for exciting a compound of the present invention varies depending upon the compound represented by general formula (1) and the wavelength of the excitation light is not particularly limited as long as a compound of the present invention efficiently emits light.

The wavelength is preferably, 200 to 1010 nm, more preferably 400 to 900 nm, and more preferably 480 to 800 nm. When light within a near infrared region is used, the wavelength that is used is preferably 600 to 1000 nm, and more preferably 680 to 900 nm, which is excellent in permeability through a living body.

The source of fluorescent excitation light for exciting a compound of the present invention is not particularly limited and various types of laser light sources can be used. Examples of these laser light sources include a dye laser light source, a semiconductor laser light source, an ion laser light source, a fiber laser light source, a halogen lamp, a xenon lamp and a tungsten lamp. Alternatively, if various types of optical filters are used, a favorable excitation wavelength can be obtained and fluorescence alone can be detected.

As described above, in the state where a compound of the present invention present within cancer stem cells is allowed to emit light by applying excitation light to an individual biological organism, if the cancer stem cells can be photographed, a luminescent site can be easily detected. Furthermore, if an image in light field, which is obtained by applying visible light, is combined with a fluorescent image, which is obtained by applying excitation light, with the help of an image processing unit, cancer stem cells can be more specifically observed. Furthermore, if a confocal microscope is used, a sectional optical image can be favorably obtained. Furthermore, a multiphoton excitation fluorescence microscope, since it is highly permeable to a deep portion and a spatial resolution, is favorably used for observing inside a tissue.

EXAMPLES

Now, the present invention will be more specifically described below by way of Examples. These are specific Examples for further deep understanding of the present invention and should not be construed as limiting the invention.

Example 1

Production Examples of the compounds of the present invention will be shown.

Production of compound (1)

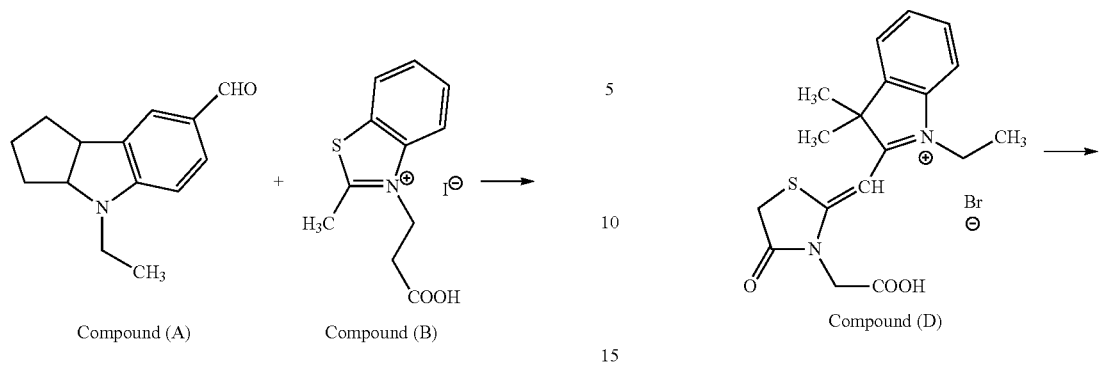

Compound (A)   Compound (B)

(1)

Compound (D)

(15)

To a solution of compound (A) (2.4 g (11.4 mmol)) in acetic acid (20 mL), compound (B) (4.0 g (11.5 mmol)) and ammonium acetate (1.6 g) were added and stirred under reflux for 2 hours. After completion of the reaction, while the reaction solution was cooled, water (50 mL) was gently added dropwise to cool the reaction solution to room temperature. The solid substance precipitated was filtered, washed twice with water (100 mL) and further washed with 2-propanol (50 mL) to obtain the desired product (1) (3.3 g) (yield 54.4%). The desired product was confirmed by $^1$H nuclear magnetic resonance spectroscopic analysis (ECA-400, manufactured by JEOL Ltd.) and LC/TOF MS (LC/MSD TOF, manufactured by Agilent Technologies).

Production of compound (15)

To a solution of compound (C) (1.4 g (5.2 mmol)) in acetic acid (20 mL), compound (D) (2.2 g (5.2 mmol)) and ammonium acetate (1.0 g) were added and stirred under reflux for 3 hours. After completion of the reaction, while the reaction solution was cooled, water (50 mL) was gently added dropwise to cool the reaction solution to room temperature. The solid substance precipitated was filtered, washed twice with water (100 mL) and further washed with 2-propanol (50 mL) to obtain the desired product (15) (1.7 g) (yield 48.7%). The desired product was confirmed by $^1$H nuclear magnetic resonance spectroscopic analysis (ECA-400, manufactured by JEOL Ltd.) and LC/TOF MS (LC/MSD TOF, manufactured by Agilent Technologies).

Production of compound (20)

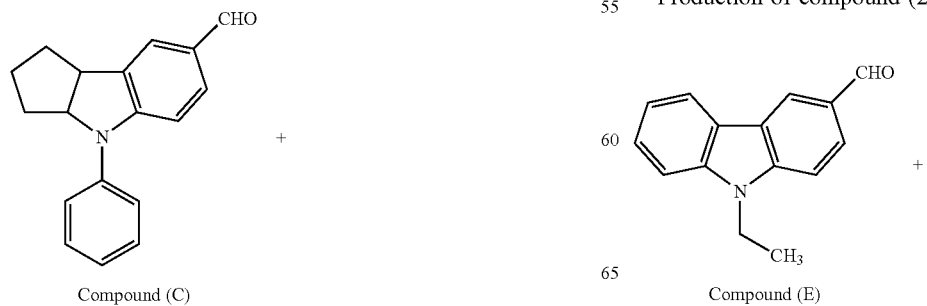

Compound (C)   Compound (E)

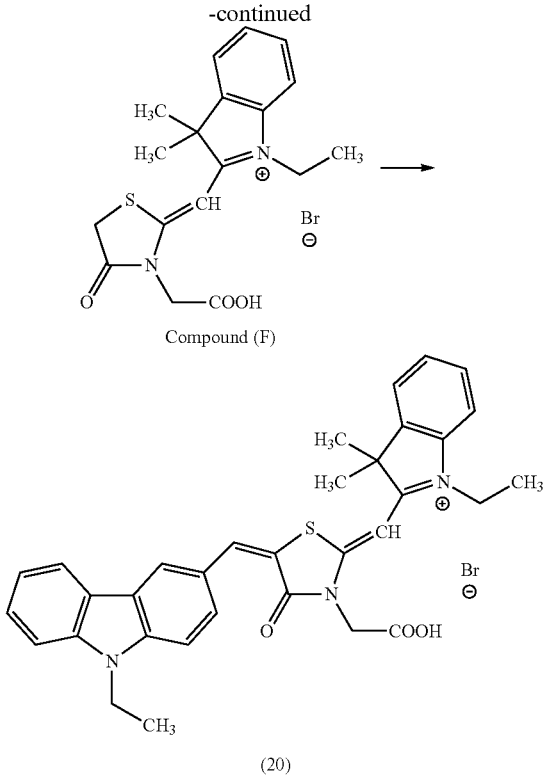

Compound (F)

(20)

To a solution of compound (E) (1.2 g (5.4 mmol)) in acetic acid (25 mL), compound (F) (2.5 g (5.9 mmol)) and ammonium acetate (1.2 g) were added and stirred under reflux for 3 hours. After completion of the reaction, while the reaction solution was cooled, water (50 mL) was gently added dropwise to cool the reaction solution to room temperature. The solid substance precipitated was filtered, washed twice with water (100 mL) and further washed with 2-propanol (50 mL) to obtain the desired product (20) (1.8 g) (yield 52.8%). The desired product was confirmed by $^1$H nuclear magnetic resonance spectroscopic analysis (ECA-400, manufactured by JEOL Ltd.) and LC/TOF MS (LC/MSD TOF, manufactured by Agilent Technologies).

Furthermore, commercially available products were purchased or 16 types of compounds shown in Table 1 below were obtained by a method according to any one of the aforementioned Production Examples. The structures of these compounds were confirmed by an analyzer in the same manner as mentioned above.

Example 2

Measurement of fluorescent property of compound A 5 μM DMSO solution of each of the compounds shown in the following Table 1 was prepared. The excitation wavelength and fluorescence wavelength of the compound were measured by a FL4500 spectrofluorometric measuring machine manufactured by Hitachi High-Technologies Corporation.

TABLE 1

| Compound | Excitation wavelength λex | Fluorescence wavelength λem |
|---|---|---|
| Compound 1 | 560 | 619 |
| Compound 5 | 582 | 678 |

TABLE 1-continued

| Compound | Excitation wavelength λex | Fluorescence wavelength λem |
|---|---|---|
| Compound 8 | 586 | 623 |
| Compound 11 | 614 | 669 |
| Compound 15 | 568 | 643 |
| Compound 20 | 493 | 585 |
| Compound 26 | 609 | 692 |
| Compound 31 | 611 | 720 |
| Compound 32 | 592 | 671 |
| Compound 33 | 560 | 677 |
| Compound 34 | 575 | 611 |
| Compound 36 | 488 | 594 |
| Compound 38 | 573 | 670 |
| Compound 39 | 591 | 626 |
| Compound 40 | 498 | 602 |
| Compound 44 | 588 | 679 |

Experimental Example 1

Observation on cancer cell inhibitory (growth suppressive) action against pancreatic cancer cells Human pancreas cancer cells, KLM-1, were pre-cultured in RPMI1640 medium containing 10% FBS at 37° C. in a 5% $CO_2$ ambient. Thereafter, 4,000 cells were seeded per well of a 96-well plate and further cultured for 24 hours. Subsequently, Compound (1) was added to the medium so as to obtain a final concentration of 10 μg/mL and cultured at 37° C. for 24 hours in a 5% $CO_2$ ambient. The cultured cells were analyzed for viable cell count according to CellTiter-Glo Luminescent Cell Viability Assay (manufactured by Promega KK.). As a reference, the number of cells cultured in a medium containing a 0.1% dimethylsulfoxide solution (hereinafter, simply referred to as DMSO) in place of a medium containing Compound (1), in the aforementioned operation, was regarded (100%).

Experimental Examples 2 to 7

Viable cell count was analyzed in the same manner as in Experimental Example 1 except that Compound (1) of Experimental Example 1 was changed to compounds shown in Table 2.

Comparative Examples 1 to 4

Viable cell count was analyzed in the same manner as in Experimental Example 1 except that Compound (1) was changed to comparative compounds 1 to 4.

Comparative Compound 1

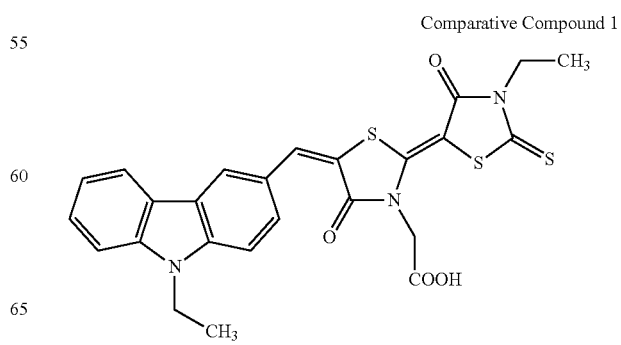

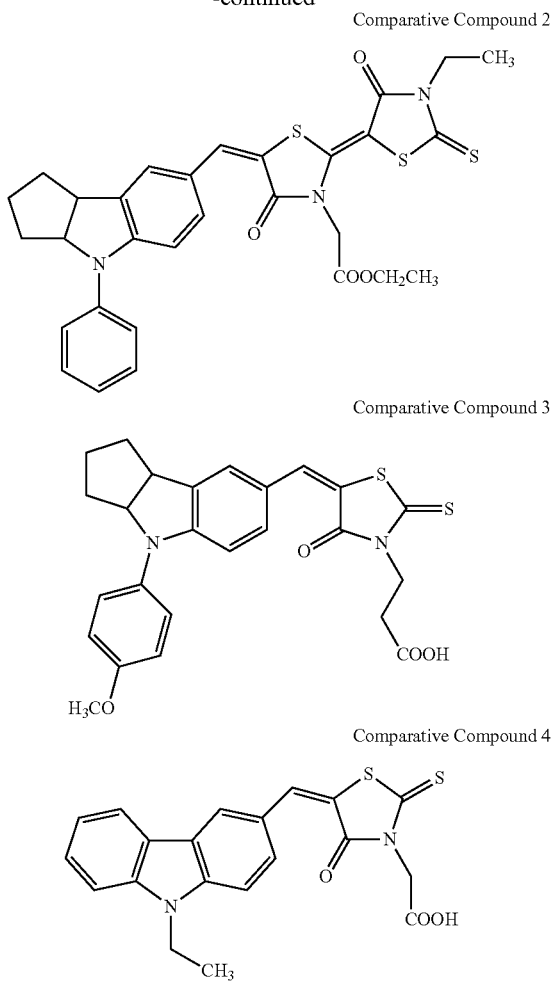

Viable cell counts of Experimental Examples 1 to 7 and Comparative Examples 1 to 4 were analyzed to obtain growth rates. The results are shown in Table 2.

Evaluation of cancer cell inhibition against the pancreatic cancer cells (KLM-1) (growth suppression) was made based on the following criteria. Note that the growth rate in Examples herein is a numerical value of the number of cells obtained after culture relative to the number of cells (regarded as 100) grown in a medium containing 0.1% DMSO. Evaluation of cancer cell inhibition against the pancreatic cancer cells (KLM-1) was made as follows.

A: Cancer cell growth rate is less than 20% (cancer cell inhibitory (growth suppressive) effect is extremely high)
B: Cancer cell growth rate is 20% or more and less than 50% (cancer cell inhibitory (growth suppressive) effect is high)
C: Cancer cell growth rate is 50% or more (cancer cell inhibitory (growth suppressive) effect is low)

TABLE 2

| | Compound | Cancer cell growth rate (%) | Evaluation |
|---|---|---|---|
| Experimental Example 1 | Compound 1 | 48.8 | B |
| Experimental Example 2 | Compound 5 | 20.8 | B |
| Experimental Example 3 | Compound 8 | 24.3 | B |
| Experimental Example 4 | Compound 11 | 2.6 | A |
| Experimental Example 5 | Compound 15 | 9.0 | A |
| Experimental Example 6 | Compound 20 | 22.3 | B |
| Experimental Example 7 | Compound 26 | 8.9 | A |
| Comparative Example 1 | Comparative compound 1 | 99.0 | C |
| Comparative Example 2 | Comparative compound 2 | 91.0 | C |
| Comparative Example 3 | Comparative compound 3 | 95.0 | C |
| Comparative Example 4 | Comparative compound 4 | 100 | C |

As is apparent from Table 2, the compounds of the present invention have a high cancer cell inhibitory (growth suppressive) effect against the pancreatic cancer cells (KLM-1), compared to the comparative compounds.

Example 3

Observation on cancer cell inhibitory (growth suppressive) action against prostatic cancer cells Experimental Example 8

Prostatic cancer cells, PC-3, were pre-cultured in RPMI1640 medium containing 10% FBS at 37° C. in a 5% $CO_2$ ambient. Thereafter, 4,000 cells were seeded per well of a 96-well plate and further cultured for 24 hours. Subsequently, Compound (11) was added to the medium so as to obtain a final concentration of 10 μg/mL and cultured at 37° C. for 24 hours in a 5% $CO_2$ ambient. The cultured cells were analyzed for viable cell count according to CellTiter-Glo Luminescent Cell Viability Assay (manufactured by Promega KK.). As a reference, the number of cells cultured in a medium containing a 0.1% dimethylsulfoxide solution (hereinafter, simply referred to as DMSO) in place of a medium containing Compound (11), in the aforementioned operation, was used as 100.

Experimental Examples 9 to 11

Viable cell count was analyzed in the same manner as in Experimental Example 8 except that the compounds shown in Table 3 were used in place of Compound (11) of Experimental Example 8.

Comparative Examples 5 to 8

Viable cell count was analyzed in the same manner as in Experimental Example 8 except that comparative compounds 1 to 4 were used in place of Compound (11) of Experimental Example 8.

The growth rate in Examples herein is a numerical value of the number of cells obtained after culture relative to the number of cells (regarded as 100) grown in a medium containing 0.1% DMSO. The results are shown in Table 3.

Evaluation of cancer cell inhibition against the prostatic cancer cells (PC-3) was made as follows.

A: Cancer cell growth rate is less than 20% (cancer cell inhibitory (growth suppressive) effect is extremely high)
B: Cancer cell growth rate is 20% or more and less than 50% (cancer cell inhibitory (growth suppressive) effect is high)
C: Cancer cell growth rate is 50% or more (cancer cell inhibitory (growth suppressive) effect is low)

TABLE 3

| | Compound | Cancer cell growth rate (%) | Evaluation |
|---|---|---|---|
| Experimental Example 8 | Compound 11 | 6.7 | A |
| Experimental Example 9 | Compound 15 | 7.1 | A |
| Experimental Example 10 | Compound 20 | 4.8 | A |
| Experimental Example 11 | Compound 26 | 5.8 | A |
| Comparative Example 5 | Comparative compound 1 | 104 | C |
| Comparative Example 6 | Comparative compound 2 | 88.8 | C |
| Comparative Example 7 | Comparative compound 3 | 86.5 | C |
| Comparative Example 8 | Comparative compound 4 | 99.9 | C |

As is apparent from Table 3, the compounds of the present invention have a high cancer cell inhibitory (growth suppressive) effect against the prostatic cancer cells (PC-3), compared to comparative compounds.

Example 4

Observation on cancer stem-cell selective inhibitory action against chronic myelocytic leukemia cells Experimental Examples 12

Human chronic myelocytic leukemia cells, K562, were pre-cultured in RPMI1640 medium containing 10% FBS at 37° C. in a 5% $CO_2$ ambient. Then, a fraction containing 80% or more of cancer stem cells was extracted by use of ALDEFLUOR reagent (manufactured by VERITAS Corporation) and FACSAria flow cytometry (manufactured by Nippon Becton, Dickinson and Company). Subsequently, Compound (5) was added to the medium so as to obtain a final concentration of 10 μg/mL and cultured at 37° C. for 24 hours in a 5% $CO_2$ ambient. The cultured cells were analyzed for viable cell count according to CellTiter-Glo Luminescent Cell Viability Assay (manufactured by Promega KK.). As a reference, the number of cells cultured in a medium containing a 0.1% dimethylsulfoxide solution (hereinafter, simply referred to as DMSO) in place of a medium containing Compound (1), in the aforementioned operation, was used as 0.1. Note that hereinafter, an ALDEFLUOR reagent positive fraction (deemed as cancer stem cells) is represented by ALDH (+), whereas an ALDEFLUOR reagent negative fraction (not deemed as cancer stem cells) is represented by ALDH (−), in some cases.

Experimental Examples 13 to 27

The same operation as in Experimental Example 12 was repeated except that Compound (5) in Experimental Example 12 was changed to the compounds shown in Table 4 and final concentrations shown in Table 4 were used and viable cell counts were separately analyzed. Note that the growth rate in Examples herein is a numerical value of the number of cells obtained after culture relative to the number of cells (regarded as 0.1) grown in a medium containing 0.1% DMSO.

Comparative Examples 9 to 15

The same operation as in Experimental Example 12 was repeated except that Compound (5) in Experimental Example 12 was changed to Imatinib (manufactured by NOVARTIS), which is a general anticancer drug, and comparative compounds shown in Table 4 and final concentrations shown in Table 4 were used and viable cell counts were separately analyzed.

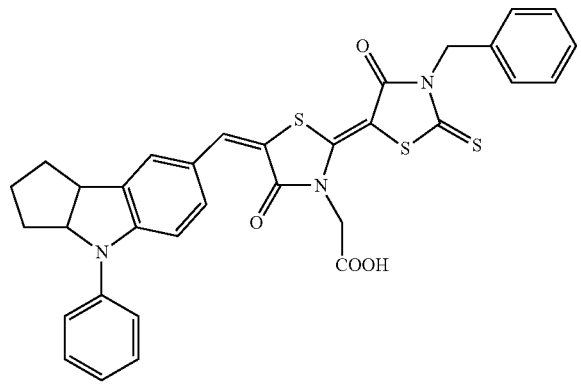

Comparative Compound 5

The results of Experimental Examples 12 to 27 and Comparative Examples 9 to 15 are collectively shown in Table 4. The growth suppressive effect of cancer stem cells was evaluated based on the following criteria. Note that the growth rate in Examples herein is a numerical value relative to the number of cells (regarded as 0.1) grown in a medium containing 0.1% DMSO.

A: The value of ALDH (+) is less than 0.5 (growth suppressive effect against cancer stem cells is extremely high)
B: The value of ALDH (+) is 0.5 or more and less than 0.95 (growth suppressive effect against cancer stem cells is high)
C: The value of ALDH (+) is 0.95 or more (no growth suppressive effect against cancer stem cells)

Furthermore, superiority of cancer stem cells was evaluated by comparing cancer stem cells to cancer cells based on the following criteria. ALDH (+) represents cancer stem cells; whereas ALDH (−) represents general cancer cells.

A: The value of ALDH (+)/ALDH (−) is less than 0.8 (selective inhibitory effect against cancer stem cells is extremely high)
B: The value of ALDH (+)/ALDH (−) is 0.8 or more and less than 0.95 (selective inhibitory effect against cancer stem cells is high)
C: The value of ALDH (+)/ALDH (−) is 0.95 or more (no selective inhibitory effect against cancer stem cells)

TABLE 4

| | Compound | Amount of dye | ALDH(+) | Growth suppression evaluated | ALDH(−) | ALDH(+)/ ALDH(−) | ALDH(+) Superiority evaluation |
|---|---|---|---|---|---|---|---|
| Experimental Example 12 | 5 | 10 μg/ml | 0.35 | A | 0.40 | 0.88 | B |
| Experimental Example 13 | 8 | 10 μg/ml | 0.23 | A | 0.32 | 0.72 | A |

TABLE 4-continued

| | Compound | Amount of dye | ALDH(+) | Growth suppression evaluated | ALDH(−) | ALDH(+)/ALDH(−) | ALDH(+) Superiority evaluation |
|---|---|---|---|---|---|---|---|
| Experimental Example 14 | 11 | 0.05 μg/mL | 0.65 | B | 0.77 | 0.85 | B |
| Experimental Example 15 | 11 | 0.5 μg/mL | 0.32 | A | 0.49 | 0.65 | A |
| Experimental Example 16 | 11 | 1 μg/mL | 0.12 | A | 0.22 | 0.56 | A |
| Experimental Example 17 | 20 | 10 μg/ml | 0.14 | A | 0.25 | 0.56 | A |
| Experimental Example 18 | 15 | 10 μg/ml | 0.21 | A | 0.26 | 0.81 | B |
| Experimental Example 19 | 32 | 10 μg/ml | 0.78 | B | 0.90 | 0.87 | B |
| Experimental Example 20 | 33 | 10 μg/ml | 0.90 | B | 1.01 | 0.89 | B |
| Experimental Example 21 | 34 | 10 μg/ml | 0.17 | A | 0.24 | 0.69 | A |
| Experimental Example 22 | 36 | 10 μg/ml | 0.13 | A | 0.20 | 0.66 | A |
| Experimental Example 23 | 38 | 10 μg/ml | 0.05 | A | 0.11 | 0.46 | A |
| Experimental Example 24 | 39 | 10 μg/ml | 0.06 | A | 0.13 | 0.42 | A |
| Experimental Example 25 | 40 | 10 μg/ml | 0.06 | A | 0.13 | 0.41 | A |
| Experimental Example 26 | 40 | 1 μg/mL | 0.73 | B | 0.85 | 0.86 | B |
| Experimental Example 27 | 44 | 10 μg/ml | 0.03 | A | 0.11 | 0.31 | A |
| Comparative Example 9 | Imatinib | 0.12 μg/ml | 0.74 | B | 0.51 | 1.47 | C |
| Comparative Example 10 | Imatinib | 0.24 μg/ml | 0.59 | B | 0.40 | 1.48 | C |
| Comparative Example 11 | Imatinib | 0.35 μg/ml | 0.48 | A | 0.32 | 1.51 | C |
| Comparative Example 12 | Imatinib | 0.47 μg/ml | 0.36 | A | 0.22 | 1.63 | C |
| Comparative Example 13 | Imatinib | 0.59 μg/ml | 0.31 | A | 0.11 | 2.80 | C |
| Comparative Example 14 | Comparative compound 5 | 1 μg/mL | 1.06 | C | 0.97 | 1.09 | C |
| Comparative Example 15 | Comparative compound 5 | 10 μg/ml | 1.07 | C | 0.90 | 1.18 | C |

As is apparent from Table 4, it is confirmed that the compounds of the present invention has a selective inhibitory effect against cancer stem cells. More specifically, when a general anticancer agent, Imatinib, was used, an inhibitory effect against general cancer cells was observed; however, no inhibitory effect was confirmed when comparative compounds were used.

Example 5

Cancer stem-cell selective staining to chronic myelocytic leukemia cells

Experimental Example 28

The cells cultured for 24 hours in Experimental Example 16 were subjected to nuclear staining with Hoechest33342 (manufactured by Dojindo Laboratories) and a fluorescent image observed under AXIOVERT200M inverted fluorescent microscope (manufactured by Carl Zeiss) was photographed. The ratio of ALDH (+)cells stained and the ratio (percentage) of ALDH (−) cells stained in each compound are shown in Table 5.

TABLE 5

| | Compound | ALDH(+) | ALDH(−) | Selective staining of cancer stem cells |
|---|---|---|---|---|
| Experimental Example 28 | 11 | 76.7 | 48.5 | ALDH (+) cells are selectively stained |

As is apparent from Table 5, it is found that the compound of the present invention selectively stains cancer stem cells (ALDH (+)) than general cancer cells (ALDH (−)).

Example 6

Confirmation of cancer metastasis suppressive effect in cancer cell metastatic foci (region within 300 to 450 μm from a transplanted tumor)

Experimental Example 29

From cell strain K562-BFP, which is a strain of human chronic myelocytic leukemia cells having fluorescent protein TagBFP constantly expressed, a fraction (ALDH (+)) containing 80% or more of cancer stem cells was extracted by use of a cancer stem cell marker, ALDEFLUOR reagent (manufactured by VERITAS Corporation) and FACSAria flow cytometry (manufactured by Nippon Becton, Dickinson and Company). The ALDH (+) fraction and a ALDH (−) fraction of general cancer cells were transplanted separately to zebra young fish (MieKomachi lineage, 2 days after fertilization) and the fish were raised in a 32° C. environment. Furthermore, 24 hours after transplantation, Compound (16) was added to breeding water so as to obtain a final concentration of 0.5 μm and fish were raised for two days in a 32° C. environment. Cells transplanted to the zebra young fish were observed under MZ16F fluorescent stereoscopic microscope (manufactured by Leica Microsystems) and a fluorescent image of the cells after 24 hours was photographed and then fluorescent intensity was quantified.

As a reference, the fluorescent intensity of cells, which were cultured in the same operation method as above in a medium containing a 0.1% DMSO solution in place of Compound (16), was used.

Comparative Examples 16 and 17

Fluorescent images were photographed in the same manner as in Experimental Example 29 except that Imatinib and Dasatinib were respectively used in place of the compound (16) in Experimental Example 29. The cancer cell inhibition rates of metastatic foci (region within 300 to 450 μm from a transplanted tumor) of cancer cells transplanted to zebra young fish in Experimental Example 29 and Comparative Examples 16 and 17 are shown in Table 6.

The inhibition rate herein was obtained according to the expression: 100×(1−F1/F0), where the fluorescent intensity of cells when a test substance was added is represented by F1, and the fluorescent intensity of cells when a reference substance (DMSO) was added is represented by F0.

The growth suppressive effect in metastatic foci (region within 300 to 450 μm from a transplanted tumor) of cancer stem cells was evaluated based on the following criteria.

A: Inhibition rate is 70 or more (growth suppressive effect against metastatic foci (region within 300 to 450 μm from a transplanted tumor) of cancer stem cells is extremely high)

B: Inhibition rate is 50 or more and less than 70 (growth suppressive effect against metastatic foci (region within 300 to 450 μm from a transplanted tumor) of cancer stem cells is high)

C: Inhibition rate is less than 50 (growth suppressive effect against metastatic foci (region within 300 to 450 μm from a transplanted tumor) of cancer stem cells is low)

TABLE 6

|  | Compound | Inhibition rate | Evaluation |
| --- | --- | --- | --- |
| Example 29 |  | 16 |  |
| Comparative Example 16 | Imatinib | 60 | B |
| Comparative Example 17 | Dasatinib | 36 | C |

As is apparent from Table 6, it was confirmed that the cancer stem-cell inhibition drug of the present invention has a higher metastasis suppressive effect than known anticancer agents used as comparison.

INDUSTRIAL APPLICABILITY

The compound provided by the present invention is useful as a cancer cell inhibitory drug. Furthermore, owing to the cancer cell inhibitory drug provided by the present invention, growth suppression, cellular division suppression, metastasis suppression, functional inhibition and cytocidal action of cancer cells, particularly cancer stem cells, can be mediated. In addition, cancer stem cells can be easily detected and the site of cancer stem cells can be accurately specified. The compound of the present invention is expected to widely contribute to the medical industry.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A method of inhibiting growth of a cancer cell, which is at least one selected from the group consisting of a pancreatic cancer cell, a prostatic cancer cell, and a chronic myelocytic leukemia cell, in a subject in need thereof, the method comprising administering to the subject a composition comprising, as an active ingredient, a compound represented by general formula (1):

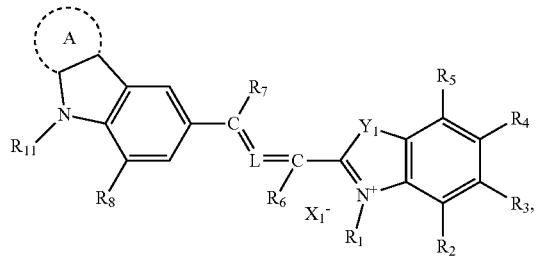

(1)

where $R_1$ independently represents an alkyl group, a carboxylalkyl group, an alkoxycarbonylalkyl group, or an alkylcarbonyloxyalkyl group; $R_2$ to $R_5$ each independently represents a hydrogen atom, an alkyl group, an aryl group, an alkoxy group, a halogen atom, an alkoxysulfonyl group, a N-alkylsulfamoyl group, an alkyloxycarbonyl group, or a N-alkylcarbamoyl group; $R_6$ and $R_7$ each independently represents a hydrogen atom, an alkyl group, or a phenyl group; $R_8$ represents a hydrogen atom, an alkyl group, an alkenyl group, or a halogen atom; $R_{11}$ represents an alkyl group, an aryl group, or an aralkyl group; $X_1^-$ represents an anionic group;

A represents a cyclopentane ring or a benzene ring;

$Y_1$ represents an oxygen atom, a sulfur atom, a nitrogen atom binding to an alkyl group or —$C(R_{12})(R_{13})$—, where $R_{12}$ and $R_{13}$ each independently represents an alkyl group, or $R_{12}$ and $R_{13}$ bind together to form an aliphatic ring; and L is absent and carbons at both sides of L are bound through a double bond, is represented by general formula (2), or represents =$C(R_{15})$—$C(R_{16})$=, where $R_{15}$ and $R_{16}$ each independently represents a hydrogen atom or an alkyl group:

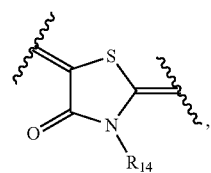

(2)

where $R_{14}$ represents an alkyl group, a carboxylalkyl group, an alkoxycarbonylalkyl group, or an alkylcarbonyloxyalkyl group.

2. The method according to claim 1, wherein the compound represented by the general formula (1) is a compound represented by general formula (3):

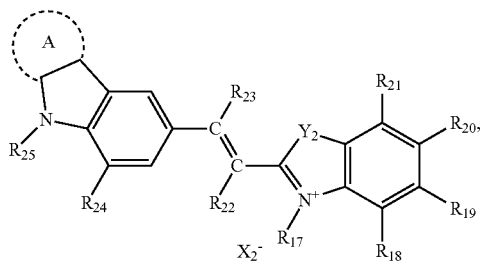

(3)

where $R_{17}$ each independently represents an alkyl group, a carboxylalkyl group, an alkoxycarbonylalkyl group, or an alkylcarbonyloxyalkyl group; $R_{18}$ to $R_{21}$ each independently represents a hydrogen atom, an alkyl group, an aryl group, an alkoxy group, a halogen atom, an alkoxysulfonyl group, a N-alkylsulfamoyl group, an alkyloxycarbonyl group, or a N-alkylcarbamoyl group; $R_{22}$ and $R_{23}$ each independently represents a hydrogen atom, an alkyl group, or a phenyl group; $R_{24}$ represents a hydrogen atom or a halogen atom; $R_{25}$ represents an alkyl group, an aryl group, or an aralkyl group; $X_2^-$ represents an anionic group;

$Y_2$ represents an oxygen atom, a sulfur atom, a nitrogen atom binding to an alkyl group, or —$C(R_{26})(R_{27})$—, where $R_{26}$ and $R_{27}$ each independently represents an alkyl group, or $R_{26}$ and $R_{27}$ bind together to form an aliphatic ring; and A represents a cyclopentane ring or a benzene ring.

3. The method according to claim 1, wherein the compound represented by the general formula (1) is a compound represented by general formula (4):

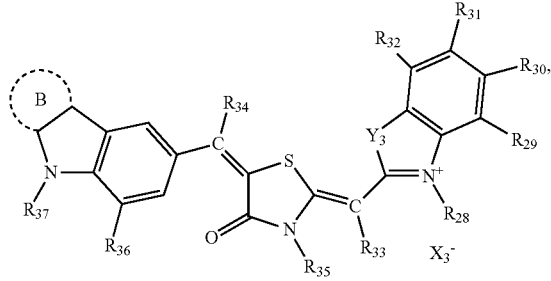

(4)

where $R_{28}$ each independently represents an alkyl group, a carboxylalkyl group, an alkoxycarbonylalkyl group, or an alkylcarbonyloxyalkyl group; $R_{29}$ to $R_{32}$ each independently represents a hydrogen atom, an alkyl group, an aryl group, an alkoxy group, a halogen atom, an alkoxysulfonyl group, a N-alkylsulfamoyl group, an alkyloxycarbonyl group, or a N-alkylcarbamoyl group; $R_{33}$ and $R_{34}$ each independently represents a hydrogen atom, an alkyl group, or a phenyl group; $R_{35}$ represents an alkyl group, a carboxylalkyl group, an alkoxycarbonylalkylgroup, or an alkylcarbonyloxyalkyl group; $R_{36}$ represents a hydrogen atom or a halogen atom; $R_{37}$ represents an alkyl group, an aryl group, or an aralkyl group; $X_3^-$ represents an anionic group;

$Y_3$ represents an oxygen atom, a sulfur atom, a nitrogen atom binding to an alkyl group or —$C(R_{38})(R_{39})$—, where $R_{38}$ and $R_{39}$ each independently represents an alkyl group, or $R_{38}$ and $R_{39}$ bind together to form an aliphatic ring; and B represents a cyclopentane ring or a benzene ring.

4. The method according to claim 1, wherein the compound represented by the general formula (1) is a compound having a luminescence property.

5. The method according to claim 1, wherein the pancreatic cancer cell, the prostatic cancer cell, or the chronic myelocytic leukemia cell is a cancer stem cell.

6. The method according to claim 1, wherein the cancer cell is the chronic myelocytic leukemia cell.

7. The method according to claim 1, wherein the subject is a human.

8. A method for detecting a composition taken into a cancer cell in a subject in need thereof, comprising:

administering to the subject a composition; and detecting light emitted from the composition taken into the cancer cell, wherein the cancer cell is at least one selected from the group consisting of a pancreatic cancer cell, a prostatic cancer cell, and a chronic myelocytic leukemia cell, wherein the composition comprises, as an active ingredient, a compound represented by general formula (1):

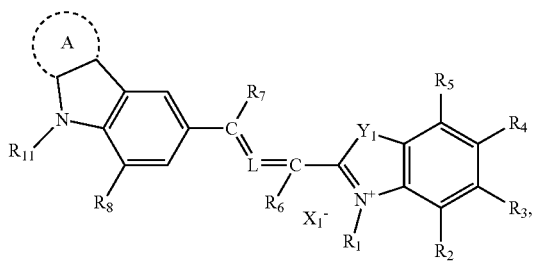

(1)

where $R_1$ independently represents an alkyl group, a carboxylalkyl group, an alkoxycarbonylalkyl group, or an alkylcarbonyloxyalkyl group; $R_2$ to $R_5$ each independently represents a hydrogen atom, an alkyl group, an aryl group, an alkoxy group, a halogen atom, an alkoxysulfonyl group, a N-alkylsulfamoyl group, an alkyloxycarbonyl group, or a N-alkylcarbamoyl group; $R_6$ and $R_7$ each independently represents a hydrogen atom, an alkyl group, or a phenyl group; $R_8$ represents a hydrogen atom, an alkyl group, an alkenyl group, or a halogen atom; $R_{11}$ represents an alkyl group, an aryl group, or an aralkyl group; $X_1^-$ represents an anionic group;

A represents a cyclopentane ring or a benzene ring;

$Y_1$ represents an oxygen atom, a sulfur atom, a nitrogen atom binding to an alkyl group or —$C(R_{12})(R_{13})$—, where $R_{12}$ and $R_{13}$ each independently represents an alkyl group, or $R_{12}$ and $R_{13}$ bind together to form an aliphatic ring; and L is absent and carbons at both sides of L are bound through a double bond, is represented by general formula (2), or represents =$C(R_{15})$—$C(R_{16})$=, where $R_{15}$ and $R_{16}$ each independently represents a hydrogen atom or an alkyl group:

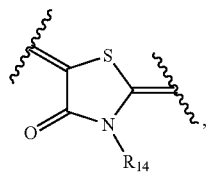

(2)

where $R_{14}$ represents an alkyl group, a carboxylalkyl group, an alkoxycarbonylalkyl group, or an alkylcarbonyloxyalkyl group.

9. The method according to claim 8, wherein the compound represented by the general formula (1) is a compound represented by general formula (3):

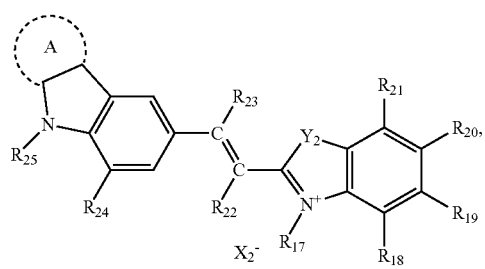

(3)

where $R_{17}$ each independently represents an alkyl group, a carboxylalkyl group, an alkoxycarbonylalkyl group, or an alkylcarbonyloxyalkyl group; $R_{18}$ to $R_{21}$ each independently represents a hydrogen atom, an alkyl group, an aryl group, an alkoxy group, a halogen atom, an alkoxysulfonyl group, a N-alkylsulfamoyl group, an alkyloxycarbonyl group, or a N-alkylcarbamoyl group; $R_{22}$ and $R_{23}$ each independently represents a hydrogen atom, an alkyl group, or a phenyl group; $R_{24}$ represents a hydrogen atom or a halogen atom; $R_{25}$ represents an alkyl group, an aryl group, or an aralkyl group; $X_2^-$ represents an anionic group;

$Y_2$ represents an oxygen atom, a sulfur atom, a nitrogen atom binding to an alkyl group, or —$C(R_{26})(R_{27})$—, where $R_{26}$ and $R_{27}$ each independently represents an alkyl group, or $R_{26}$ and $R_{27}$ bind together to form an aliphatic ring; and A represents a cyclopentane ring or a benzene ring.

10. The method according to claim 8, wherein the compound represented by the general formula (1) is a compound represented by general formula (4):

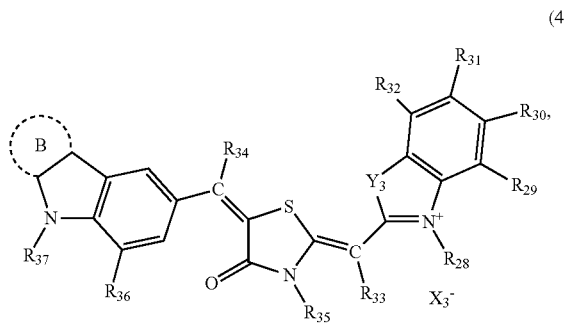

(4)

where $R_{28}$ each independently represents an alkyl group, a carboxylalkyl group, an alkoxycarbonylalkyl group, or an alkylcarbonyloxyalkyl group; $R_{29}$ to $R_{32}$ each independently represents a hydrogen atom, an alkyl group, an aryl group, an alkoxy group, a halogen atom, an alkoxysulfonyl group, a N-alkylsulfamoyl group, an alkyloxycarbonyl group, or a N-alkylcarbamoyl group; $R_{33}$ and $R_{34}$ each independently represents a hydrogen atom, an alkyl group, or a phenyl group; $R_{35}$ represents an alkyl group, a carboxylalkyl group, an alkoxycarbonylalkylgroup, or an alkylcarbonyloxyalkyl group; $R_{36}$ represents a hydrogen atom or a halogen atom; $R_{37}$ represents an alkyl group, an aryl group, or an aralkyl group; $X_3^-$ represents an anionic group;

$Y_3$ represents an oxygen atom, a sulfur atom, a nitrogen atom binding to an alkyl group, or —$C(R_{38})(R_{39})$—, where $R_{38}$ and $R_{39}$ each independently represents an alkyl group, or $R_{38}$ and $R_{39}$ bind together to form an aliphatic ring; and B represents a cyclopentane ring or a benzene ring.

11. The method according to claim 8, wherein the compound represented by the general formula (1) is a compound having a luminescence property.

12. The method according to claim 8, wherein the pancreatic cancer cell, the prostatic cancer cell, or the chronic myelocytic leukemia cell is a cancer stem cell.

13. The method according to claim 8, wherein the cancer cell is the chronic myelocytic leukemia cell.

14. The method according to claim 8, wherein the subject is a human.

15. The method according to claim 8, wherein the light is a fluorescence emitted from the composition.

16. A method of inhibiting growth of a cancer cell, which is at least one selected from the group consisting of a pancreatic cancer cell, a prostatic cancer cell, and a chronic myelocytic leukemia cell, in a subject in need thereof, the method comprising administering to the subject a composition comprising, as an active ingredient, a compound is selected form the group consisting of compounds (1), (5), (8), (11), (32), (33), (34), (36), (38), (39), (40), and (44):

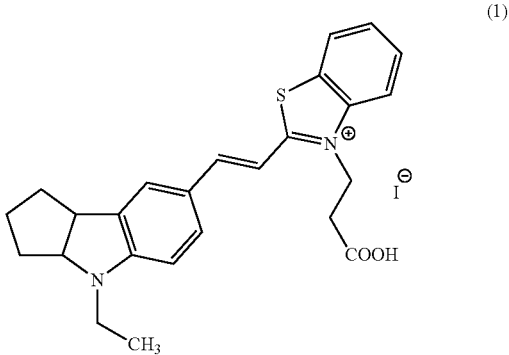

(1)

-continued
(5)
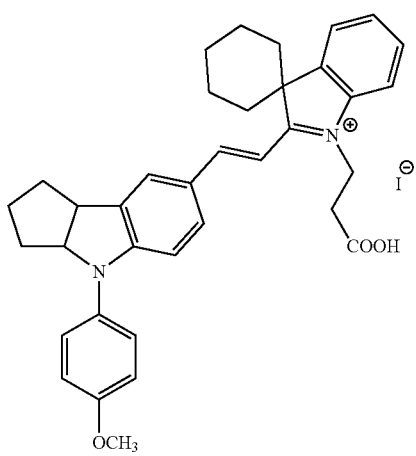
(8)
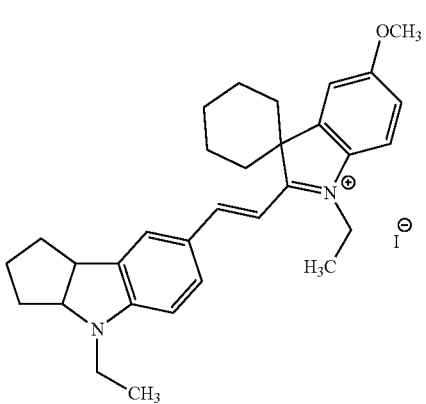
(11)
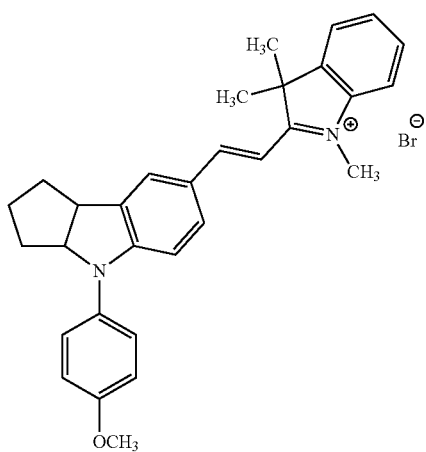
(32)
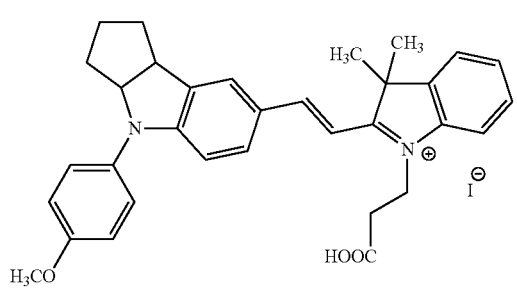
-continued
(33)
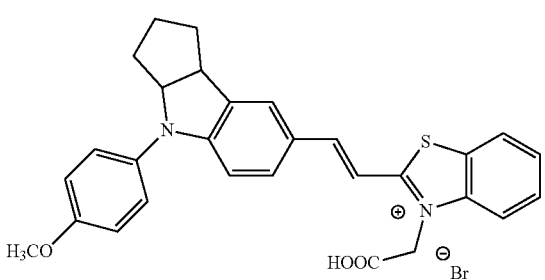
(34)
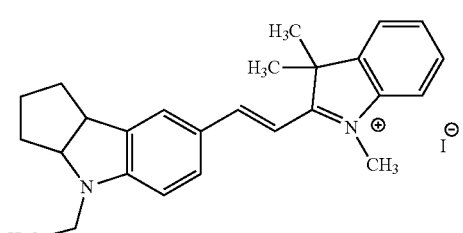
(36)
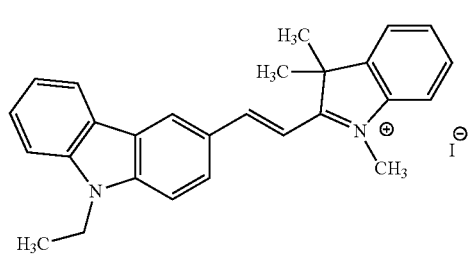
(38)
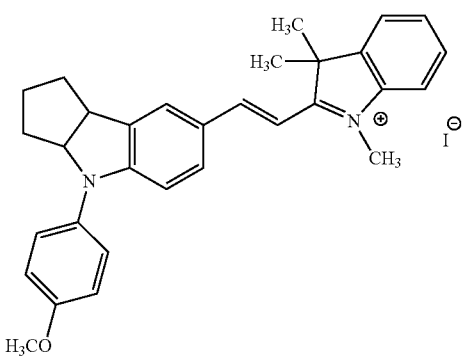
(39)
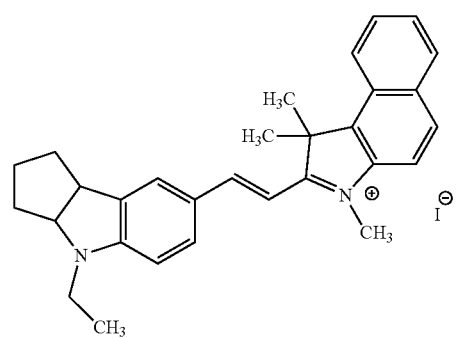

(40)

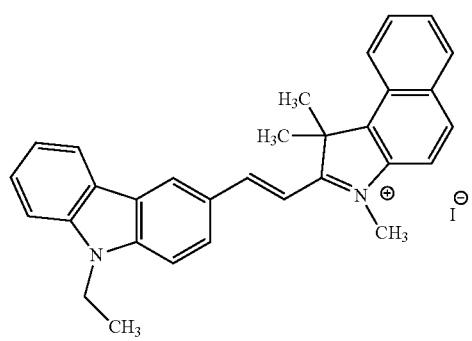

(44)

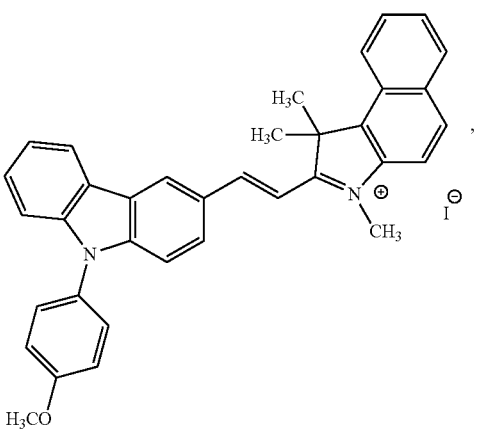

17. A method for detecting a cancer cell in a subject in need thereof, comprising:
   administering to the subject a composition; and
   detecting luminescence emitted from the cancer cell,
   wherein the cancer cell is at least one selected from the group consisting of a pancreatic cancer cell, a prostatic cancer cell, and a chronic myelocytic leukemia cell,
   wherein the subject is selected from the group consisting of an amphibian, a non-mammal, non-amphibian vertebrate animal, a bird, and a mammal, and
   wherein the composition comprises, as an active ingredient, a compound selected form the group consisting of compounds (1), (5), (8), (11), (32), (33), (34), (36), (38), (39), (40), and (44):

(1)

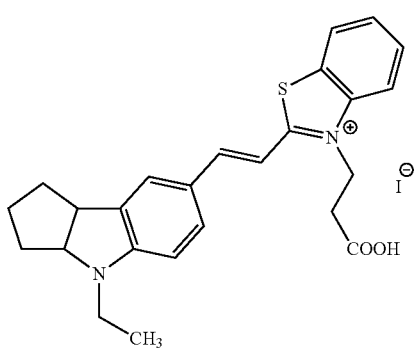

(5)

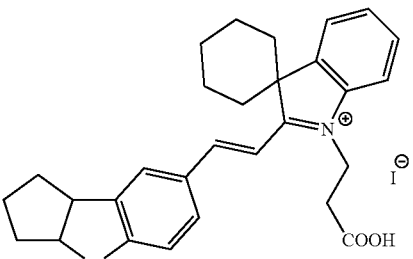

(8)

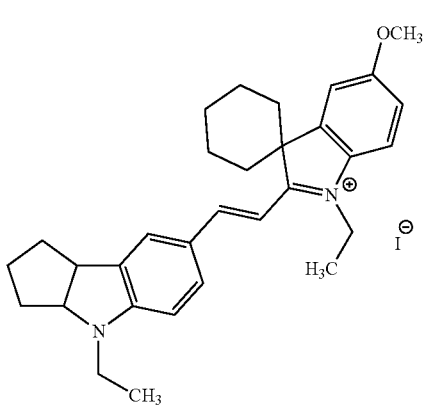

(11)

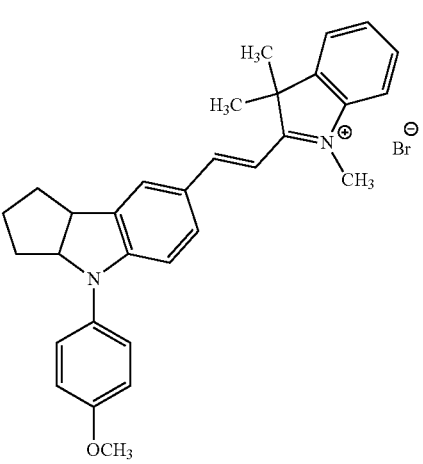

(32)

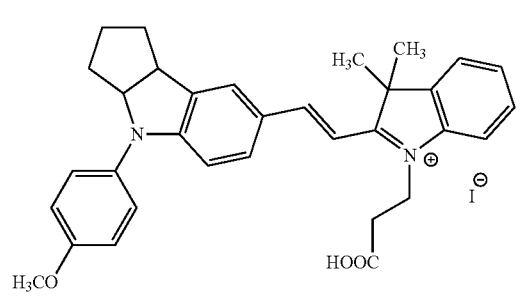

(33)
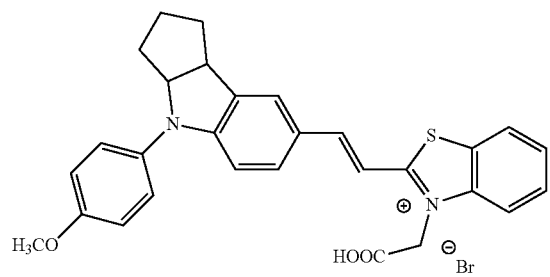
(34)
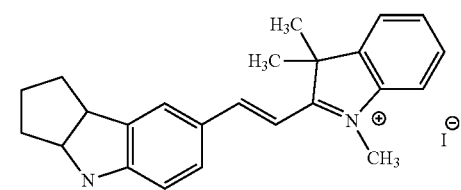
(36)
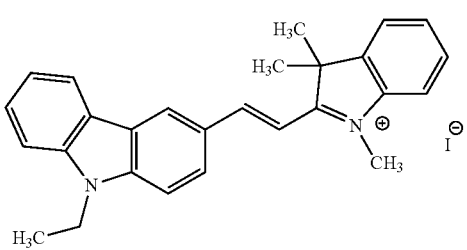
(38)
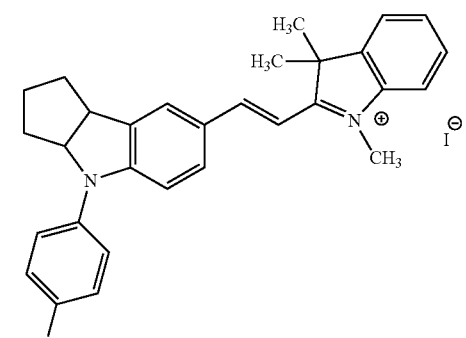
(39)
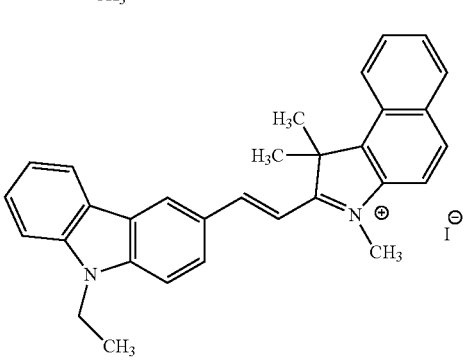
(40)
(44)
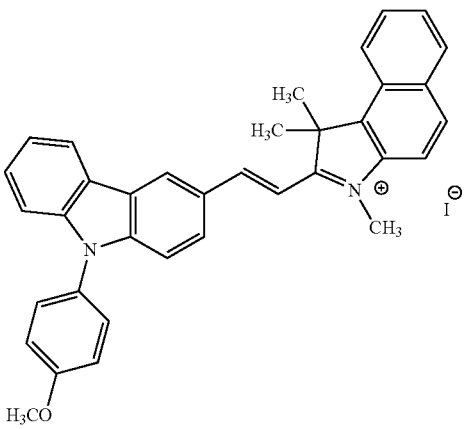
18. The method according to claim 1, wherein the subject is a vertebrate animal, an amphibian, or a mammal.
19. The method according to claim 8, wherein the subject is a vertebrate animal, an amphibian, or a mammal.
20. The method according to claim 16, wherein the subject is a vertebrate animal, an amphibian, or a mammal.
* * * * *